United States Patent
Yonemura et al.

(10) Patent No.: US 10,916,693 B2
(45) Date of Patent: Feb. 9, 2021

(54) PIEZOELECTRIC ELEMENT AND PIEZOELECTRIC ELEMENT-BASED DEVICE

(71) Applicant: Seiko Epson Corporation, Tokyo (JP)

(72) Inventors: Takayuki Yonemura, Suwa (JP); Chikara Kojima, Matsumoto (JP); Xiaoxing Wang, Chino (JP); Tetsuya Isshiki, Shiojiri (JP); Yasuhiro Itayama, Kai (JP)

(73) Assignee: Seiko Epson Corporation

( * ) Notice: Subject to any disclaimer, the term of this patent is extended or adjusted under 35 U.S.C. 154(b) by 513 days.

(21) Appl. No.: 15/920,829

(22) Filed: Mar. 14, 2018

(65) Prior Publication Data
US 2018/0277742 A1    Sep. 27, 2018

(30) Foreign Application Priority Data

Mar. 24, 2017 (JP) .................................. 2017-058613

(51) Int. Cl.
*H01L 41/187* (2006.01)
*H01L 41/09* (2006.01)
(Continued)

(52) U.S. Cl.
CPC ............ *H01L 41/1876* (2013.01); *A61B 8/14* (2013.01); *A61B 8/4444* (2013.01);
(Continued)

(58) Field of Classification Search
CPC ............... H01L 41/1876; H01L 41/042; H01L 41/0475; H01L 41/0805; H01L 41/0973; A61B 8/461; A61B 8/4444; A61B 8/4483; A61B 8/4427; B06B 1/0692; B06B 1/0666; B41J 2/14201; B41J 2/14233;
(Continued)

(56) References Cited

U.S. PATENT DOCUMENTS

| | | | |
|---|---|---|---|
| 2005/0014850 A1* | 1/2005 | Hu .................. | B82Y 30/00 516/22 |
| 2005/0157093 A1 | 7/2005 | Murai | |

(Continued)

FOREIGN PATENT DOCUMENTS

| | | |
|---|---|---|
| JP | 2000-299510 A | 10/2000 |
| JP | 2001-223404 A | 8/2001 |

(Continued)

*Primary Examiner* — Thomas M Dougherty
(74) *Attorney, Agent, or Firm* — Harness, Dickey & Pierce, P.L.C.

(57) ABSTRACT

A piezoelectric element has a diaphragm, a first electrode on the diaphragm, a piezoelectric layer on the first electrode, and a second electrode on the piezoelectric layer. The piezoelectric layer is a stack of multiple piezoelectric films and is made of a perovskite composite oxide containing lead, zirconium, and titanium and represented by the general formula $ABO_3$, with the molar ratio of the A-site to the B-site (A/B) in the perovskite composite oxide being 1.14 or more and 1.22 or less. In current-time curve measurement, the activation energy calculated from relaxation current using an Arrhenius plot is 0.6 [eV] or less. The relaxation current is the amount of current at the time at which a downward trend in current turns upward.

8 Claims, 13 Drawing Sheets

(51) Int. Cl.
*H01L 41/047* (2006.01)
*C01G 25/00* (2006.01)
*A61B 8/00* (2006.01)
*A61B 8/14* (2006.01)
*B41J 2/14* (2006.01)
*B41J 2/16* (2006.01)
*G01N 29/24* (2006.01)
*H01L 41/04* (2006.01)
*H01L 41/08* (2006.01)
*B06B 1/06* (2006.01)
*H01L 41/47* (2013.01)

(52) U.S. Cl.
CPC .......... *A61B 8/4483* (2013.01); *A61B 8/461* (2013.01); *B06B 1/0692* (2013.01); *B41J 2/14201* (2013.01); *B41J 2/14233* (2013.01); *B41J 2/161* (2013.01); *B41J 2/1623* (2013.01); *B41J 2/1628* (2013.01); *B41J 2/1629* (2013.01); *B41J 2/1631* (2013.01); *B41J 2/1632* (2013.01); *B41J 2/1634* (2013.01); *B41J 2/1635* (2013.01); *B41J 2/1642* (2013.01); *B41J 2/1645* (2013.01); *B41J 2/1646* (2013.01); *C01G 25/006* (2013.01); *G01N 29/245* (2013.01); *H01L 41/042* (2013.01); *H01L 41/0475* (2013.01); *H01L 41/0805* (2013.01); *H01L 41/0973* (2013.01); *A61B 8/4427* (2013.01); *B06B 1/0666* (2013.01); *B41J 2002/14258* (2013.01); *B41J 2202/03* (2013.01); *C01P 2002/34* (2013.01); *C01P 2006/40* (2013.01)

(58) Field of Classification Search
CPC ........ B41J 2/161; B41J 2/1623; B41J 2/1628; B41J 2/1629; B41J 2/1631; B41J 2/1632; B41J 2/1634; B41J 2/1635; B41J 2/1642; B41J 2/1645; B41J 2/1646; B41J 2002/14258; B41J 2002/03; C01G 29/245; G01N 29/245; C01P 2002/34; C01P 2006/40
USPC ............. 310/324, 358; 252/62.9 R, 62.9 PZ; 501/134
See application file for complete search history.

(56) References Cited

U.S. PATENT DOCUMENTS

2015/0145926 A1\* 5/2015 Yonemura .......... H01L 41/1878
347/68
2016/0236470 A1 8/2016 Mizukami

FOREIGN PATENT DOCUMENTS

| JP | 2004-042329 A | 2/2004 |
| JP | 2007-042984 A | 2/2007 |
| JP | 2016-150471 A | 8/2016 |

\* cited by examiner

LOADING PULSES: VL=0 V, VH=+25 V, 50-kHz SQUARE WAVE
MEASUREMENT PULSES: VL=−25 V, VH=+25 V, 1-kHz TRIANGULAR WAVE

PIEZOELECTRIC ELEMENT AND PIEZOELECTRIC ELEMENT-BASED DEVICE

This application claims priority under 35 U.S.C. § 119 to Japanese Patent Application No. 2017-058613 filed on Mar. 24, 2017, the entire disclosure of which is expressly incorporated by reference herein.

BACKGROUND

1. Technical Field

The present invention relates to a piezoelectric element and a piezoelectric element-based device.

2. Related Art

A piezoelectric element generally has a piezoelectric layer, which has electromechanical transduction properties, and two electrodes sandwiching the piezoelectric layer. Devices in which such a piezoelectric element is used as a drive source (piezoelectric element-based devices) have been actively developed in recent years. Examples of piezoelectric element-based devices include liquid ejecting heads, typically an ink jet recording head, MEMS elements, typically a piezoelectric MEMS element, ultrasonic measuring instruments, typically an ultrasonic sensor, and piezoelectric actuator equipment.

Many of the composite oxides represented by the general formula $ABO_3$ have the perovskite crystal structure. Composite oxides having particular A- and B-site compositions act to provide electromechanical transduction. For example, lead zirconate titanate (PZT), which contains lead (Pb) at the A-site and zirconium (Zr) and titanium (Ti) at the B-site, is used as piezoelectric material suitable for ink jet recording heads (for example, see JP-A-2000-299510 and JP-A-2001-223404). In the field of ink jet recording heads, demand for high piezoelectric properties of piezoelectric elements has been growing in recent years in concert with improving performance of electrical equipment.

In the fabrication of a piezoelectric element in which a PZT thin film is used as a piezoelectric material, however, an overage of Pb needs to be added in advance, or defects such as lattice imperfections would occur because of the evaporation of lead oxides ($PbO_X$), affecting the piezoelectric properties. A PZT thin film usually has grain boundaries and other lattice imperfections between columnar grains. The addition of an overage of Pb therefore leads to Pb atoms in the form of $PbO_X$ entering into the grain boundaries or other spaces. Thus, adjusting the overage of Pb to within an appropriate range improves the piezoelectric properties (e.g., displacement) by reducing lattice imperfections.

However, it is difficult to improve the piezoelectric properties by controlling lattice imperfections through direct quantification of them. Such a problem is not limited to ink jet recording and other liquid ejecting heads. Similar problems may also be encountered with other piezoelectric element-based devices.

SUMMARY

An advantage of some aspects of the invention is that they provide a piezoelectric element that achieves high piezoelectric properties owing to fewer lattice imperfections and a piezoelectric element-based device.

To attain this advantage, the inventors focused their attention to electric charges resulting from defects in a PZT thin film. That is, the inventors found that since movement of such charges in a PZT thin film caused by imprint pulses produces an electric field, the impact of lattice imperfections can be indirectly read from changes in characteristics, such as activation energy. The present invention is based on these findings.

According to an aspect of the invention, a piezoelectric element has a diaphragm, a first electrode on the diaphragm, a piezoelectric layer on the first electrode, and a second electrode on the piezoelectric layer. The piezoelectric layer is a stack of multiple piezoelectric films and is made of a perovskite composite oxide containing lead, zirconium, and titanium and represented by the general formula $ABO_3$, with the molar ratio of the A-site to the B-site (A/B) in the perovskite composite oxide being 1.14 or more and 1.22 or less. In current-time curve measurement, the activation energy calculated from relaxation current using an Arrhenius plot is 0.6 [eV] or less. The relaxation current is the amount of current at the time at which a downward trend in current turns upward.

By virtue of the optimum overage of lead selected for the lower-activation-energy range, this aspect provides a piezoelectric element that has a piezoelectric layer that achieves high piezoelectric properties owing to fewer lattice imperfections.

It is preferred in this piezoelectric element that the molar ratio of the A-site to the B-site (A/B) in the perovskite composite oxide be 1.16 or more and 1.20 or less, and that the activation energy be 0.5 [eV] or less.

In this case, the piezoelectric layer in the piezoelectric element achieves high piezoelectric properties owing to even fewer lattice imperfections.

Moreover, it is preferred in this piezoelectric element that the relationship between the thickness $T_p$ of the piezoelectric layer and the total thickness $T_b$ of the diaphragm and first electrode satisfy formula (1), and that electromechanical coupling coefficient k calculated from formula (2), where $f_a$ is the frequency [MHz] at which the impedance peaks and $f_r$ is the frequency [MHz] at which the impedance bottoms out, be 0.278 or more.

$$0.47 < T_p/T_b < 1.33 \tag{1}$$

$$k^2 = (f_a^2 - f_r^2)/(f_a^2) \tag{2}$$

In this case, the piezoelectric layer is thin enough to improve the piezoelectric properties but without affecting the force generated for deforming the diaphragm. The piezoelectric element therefore has a piezoelectric layer that achieves higher piezoelectric properties.

Moreover, it is preferred in this piezoelectric element that the relationship between the thickness of the piezoelectric layer, diaphragm, and first electrode satisfy formula (3), and that the electromechanical coupling coefficient k calculated from formula (2) be 0.284 or more.

$$0.51 < T_p/T_b < 1.15 \tag{3}$$

In this case, the piezoelectric layer in the piezoelectric element achieves higher piezoelectric properties.

According to another aspect of the invention, a piezoelectric element-based device includes such a piezoelectric element.

This aspect provides a piezoelectric element-based device stable in terms of piezoelectric and dielectric properties and superior in drive properties.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
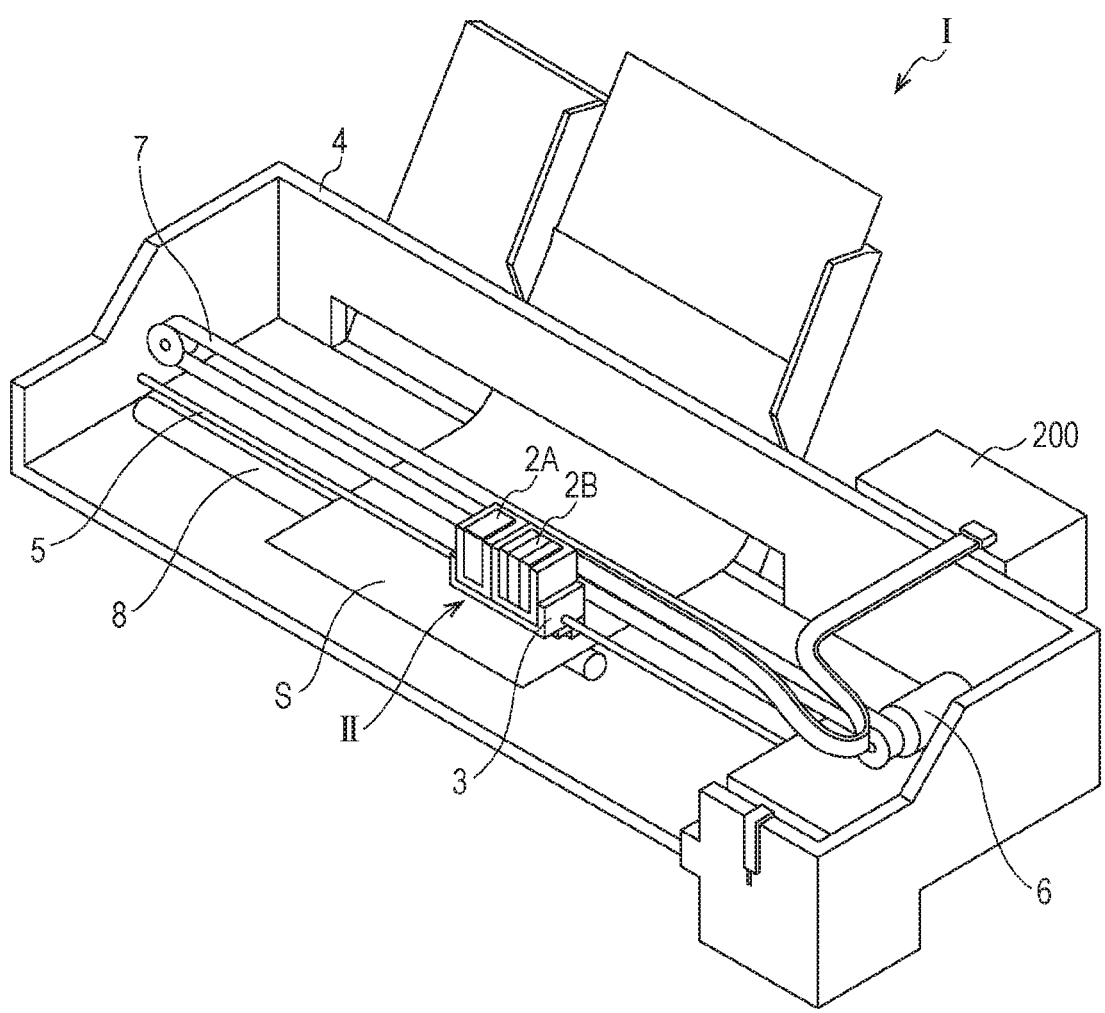
FIG. 1 is a schematic perspective view of an ink jet recording apparatus.

The following describes embodiments of the invention with reference to the drawings. The following description only illustrates an aspect of the invention, and changes can be made within the scope of the aspect of the invention. In the drawings, like elements are referenced by like numerals so that duplicate descriptions can be avoided. The letters X, Y, and Z refer to three spatial axes that extend perpendicular to one another. The directions along these axes are herein referred to as the first direction X (X direction), the second direction Y (Y direction), and the third direction Z (Z direction). In each drawing, the direction in which an arrow points is the positive (+) direction, and the opposite is the negative (−) direction. The X and Y directions are in-plane directions based on plates, layers, and films, and the Z direction is the direction of the thickness or stacking of plates, layers, and films.

The structural details in each drawing, i.e., the shape and size of an element, the thickness of a plate, layer, or film, positional relationships, repeat units, etc., may be exaggerated for convenience in describing the aspect of the invention. The term "on" as used herein is not intended to limit the positional relationship between the elements to "directly on." For example, expressions like "a first electrode on a substrate" and "a piezoelectric layer on a first electrode" do not exclude structures in which the substrate and the first electrode or the first electrode and the piezoelectric layer have another element therebetween.

Embodiment 1

Liquid Ejecting Apparatus

First, an ink jet recording apparatus as an example of a liquid ejecting apparatus is described with reference to drawings.

FIG. 1 is a schematic perspective view of an ink jet recording apparatus. As illustrated, the ink jet recording apparatus (recording apparatus) I has an ink jet recording head unit (head unit) II detachably fitted to cartridges 2A and 2B. The cartridges 2A and 2B are ink sources. The head unit II has multiple ink jet recording heads (recording heads) 1 (see FIG. 2 and other drawings), which are described hereinafter, and is on a carriage 3. The carriage 3 can move along a carriage shaft 5 installed in the main unit 4. The head unit II and carriage 3 are each configured such that, for example, a black ink composition and color ink compositions can be ejected.

The power of a motor 6 is transmitted through not-illustrated cogwheels and a timing belt 7 to the carriage 3, moving the carriage 3, with the head unit II thereon, along the carriage shaft 5. The main unit 4 also has a transport roller 8 as a transport unit, and a recording sheet S, which is a sheet of paper or any other recording medium, is transported by the transport roller 8. The transport unit for the recording sheet S does not need to be a roller and can be, for example, a belt or a drum.

Each recording head 1 has piezoelectric elements 300 (see FIG. 2 and other drawings) of flexural-deformation type (flexural-displacement piezoelectric elements) as piezoelectric actuators. The use of the piezoelectric elements 300 prevents the deterioration of the characteristics of the recording apparatus I (e.g., durability and the ejection of inks). Although this embodiment takes flexural-displacement piezoelectric elements as an example, other types of piezoelectric elements can be used unless deviating from the gist of the aspect of the invention.

Liquid Ejecting Head

Figure 2:
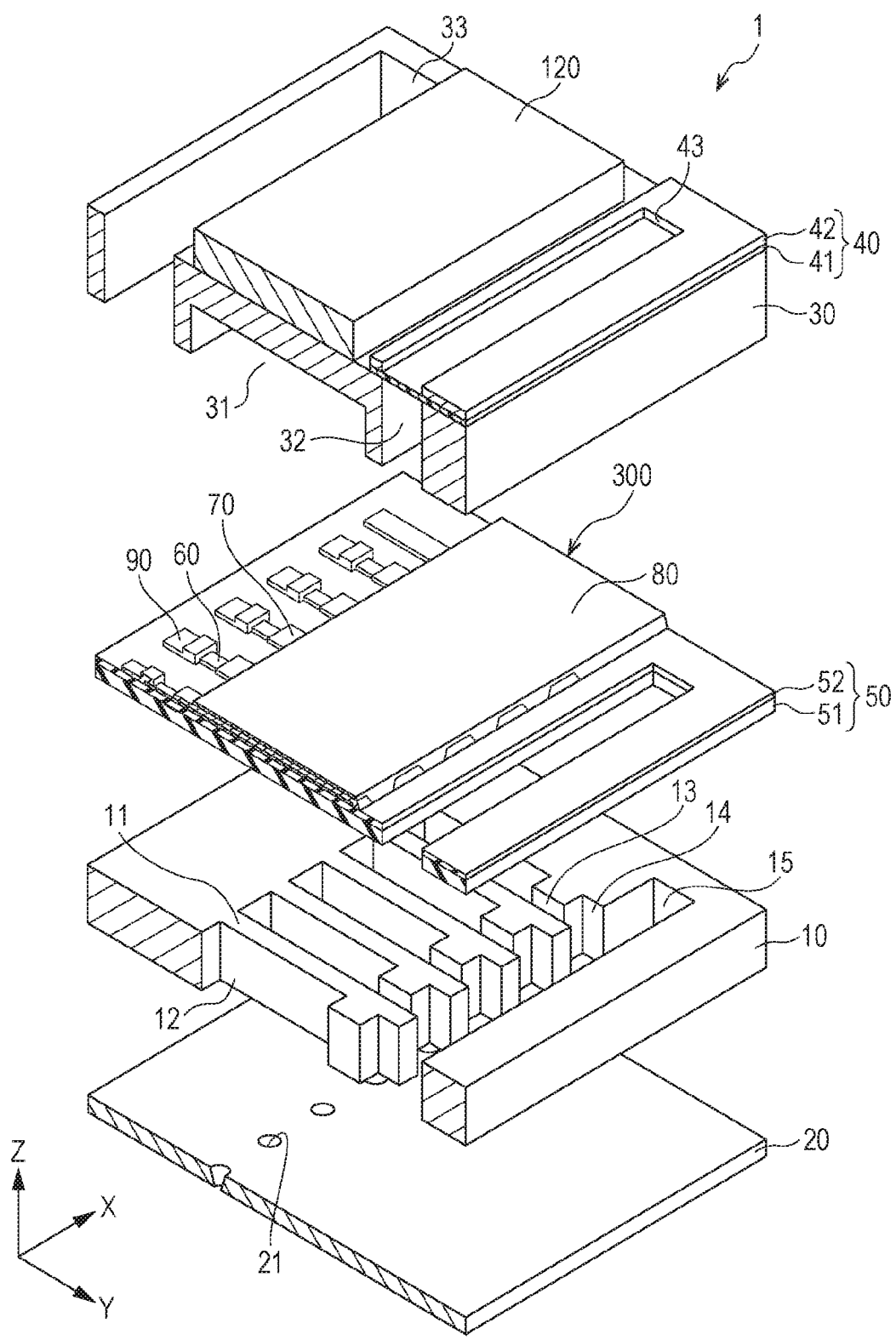
FIG. 2 is a schematic exploded perspective view of an ink jet recording head.
Figure 3:
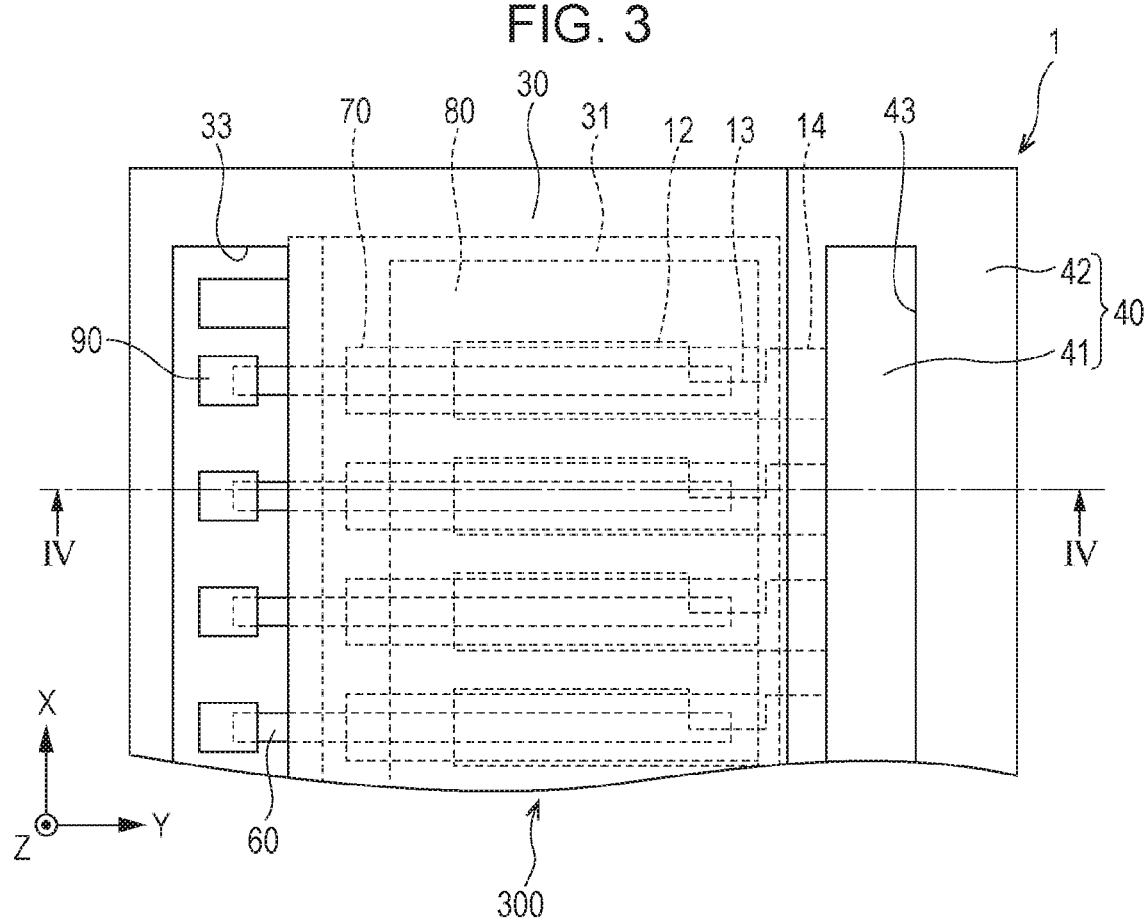
FIG. 3 is a schematic plan view of an ink jet recording head.
Figure 4:
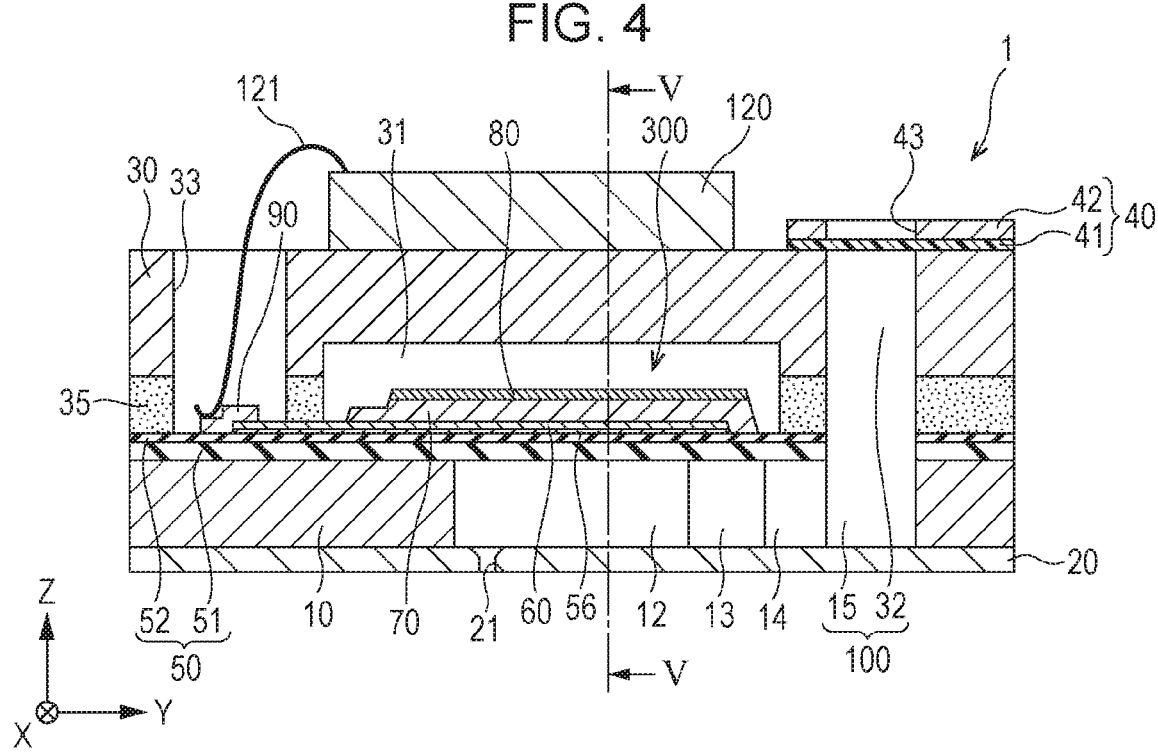
FIG. 4 is a cross-sectional diagram taken along line IV-IV of FIG. 3.

The following describes a recording head 1 as an example of a liquid ejecting head for a liquid ejecting apparatus with reference to drawings. FIG. 2 is a schematic exploded perspective view of the ink jet recording head. FIG. 3 is a schematic plan view of the ink jet recording head. FIG. 4 is a cross-sectional diagram taken along line IV-IV of FIG. 3. FIGS. 2 to 4 illustrate part of the structure of the recording head 1 and there may be omitted components.

As illustrated, the flow channel substrate (substrate) 10 is, for example, a silicon (Si) single-crystal substrate. The material for the substrate 10 does not need to be Si and can be, for example, SOI (silicon-on-insulator) or glass.

The substrate 10 has pressure chambers 12 defined by multiple walls 11. The pressure chambers 12 are lined up in the direction in which multiple nozzle openings 21 for ejecting ink of the same color are lined up (+X direction).

At the side of the ends on one side (+Y side) of the pressure chambers 12 in the substrate 10 are ink supply paths 13 and communicating paths 14. The ink supply paths 13 are configured such that the pressure chambers 12 narrow at the end on one side. The communicating paths 14 have substantially the same width, in the +X direction, as the pressure chambers 12. Outside (+Y side) the communicating paths 14 is a communicating space 15. The communicating space 15 is a component of a manifold 100, and the manifold 100 provides a common ink tank for the pressure chambers 12. The substrate 10 therefore has a liquid-flow channel formed by the pressure chambers 12, ink supply paths 13, communicating paths 14, and communicating space 15.

On one side (−Z side) of the substrate 10 is a nozzle plate 20, for example an SUS plate, joined to the substrate 10. The nozzle plate 20 has nozzle openings 21 line up in the +X direction. The nozzle openings 21 communicate one-to-one with the pressure chambers 12. The material that joins the nozzle plate 20 to the substrate 10 can be, for example, an adhesive agent or hot-melt film.

On the other side (+Z side) of the substrate 10 is a diaphragm 50. The diaphragm 50 is composed of, for example, an elastic film 51 on the substrate 10 and an insulating film 52 on the elastic film 51. The elastic film 51 is made of, for example, silicon dioxide ($SiO_2$), and the insulating film 52 is made of, for example, zirconium oxide ($ZrO_2$). The elastic film 51 does not need to be a component separate from the substrate 10. A thinned portion of the substrate 10 may serve as the elastic film 51. The elastic film 51 does not need to be a $SiO_2$ film and can be a film of, for example, aluminum oxide ($Al_2O_3$), tantalum (V) oxide ($Ta_2O_5$), or silicon nitride (SiN).

On the insulating film 52 are piezoelectric elements 300 each composed of a first electrode 60, a piezoelectric layer 70, and a second electrode 80, with a contact layer 56 interposed between the insulating film 52 and the piezoelectric elements 300. The contact layer 56, for example made of a titanium oxide ($TiO_X$), titanium (Ti), or SiN, improves adhesion between the piezoelectric layer 70 and the diaphragm 50. The contact layer 56 is optional.

When the piezoelectric material of which the piezoelectric layer 70 is made contains an alkali metal, such as potassium (K) or sodium (Na), the alkali metal may diffuse into the first electrode 60 during the formation of the piezoelectric layer 70 (described hereinafter). To address this, an insulating film 52 is provided between the first electrodes 60 and the substrate 10. The insulating film 52 serves as a barrier that prevents the alkali metal from reaching the substrate 10.

There is one first electrode 60 for each pressure chamber 12. In other words, the first electrode 60 is an independent, separate electrode provided for the pressure chamber 12. The first electrode 60 has a smaller width, in the ±X directions, than the pressure chamber 12, and has a larger width, in the ±Y directions, than the pressure chamber 12. That is, in the ±Y directions, both ends of the first electrode 60 are outside the region of the diaphragm 50 facing the pressure chamber 12. To the end on one side (the side opposite the communicating paths 14) of the first electrode 60, a lead electrode 90 is connected.

Although not provided in this embodiment, there may be a seed layer (also called an orientation-controlling layer) between the first electrode 60 and the piezoelectric layer 70, for example on the contact layer 56. The seed layer controls the orientation of crystals in the piezoelectric material of which the piezoelectric layer 70 is made. That is, providing a seed layer will ensure that the crystals in the piezoelectric material of which the piezoelectric layer 70 is made have a predetermined preferred orientation.

The piezoelectric layer 70 is between the first electrode 60 and the second electrode 80. The piezoelectric layer 70 has a larger width, in the ±X directions, than the first electrode 60, and has a larger width, in the ±Y directions, than the length, in the ±Y directions, of the pressure chamber 12. The end on the ink supply path 13 side (+Y side) of the piezoelectric layer 70 is beyond the +Y edge of the first electrode 60. That is, the +Y end of the first electrode 60 is covered with the piezoelectric layer 70. The end on the lead electrode 90 side (−Y side) of the piezoelectric layer 70 is inside (+Y side) the −Y edge of the first electrode 60. That is, the −Y end of the first electrode 60 is not covered with the piezoelectric layer 70. The piezoelectric layer 70 is a thin film of piezoelectric material having a predetermined thickness (described hereinafter).

The second electrode 80 extends continuously on the piezoelectric layers 70 and diaphragm 50 in the +X direction. That is, the second electrode 80 is a common electrode for multiple piezoelectric layers 70. In this embodiment, the first electrodes 60 are independent, separate electrodes corresponding one-to-one to the pressure chambers 12, and the second electrode 80 is a common electrode extending continuously in the direction in which the pressure chambers 12 are lined up. However, the opposite is also possible: a common first electrode 60 and separate second electrodes 80 may be used.

In this embodiment, the piezoelectric layers 70, which have electromechanical transduction properties, are displaced, and, as a result, the diaphragm 50 and first electrodes 60 are displaced. That is, the diaphragm 50 and first electrodes 60 practically function as a diaphragm. In practice, the second electrode 80 is also displaced as a result of the displacement of the piezoelectric layers 70. Therefore, the regions in which the diaphragm 50, a first electrode 60, a piezoelectric layer 70, and the second electrode 80 are stacked one after another function as moving portions (or vibrating portions) of the piezoelectric elements 300.

It should be noted that in this embodiment, one of the elastic film 51 and insulating film 52 may be omitted. In this case, the other functions as a diaphragm. It is even possible to omit both of the elastic film 51 and insulating film 52. In this case, the first electrodes 60 alone function as a diaphragm. If the first electrodes 60 are provided directly on the substrate 10, it is preferred to protect the first electrodes 60, for example with an insulating protective film, to prevent the ink from coming into contact with the first electrodes 60.

On the substrate 10 (diaphragm 50), with the piezoelectric elements 300 thereon, is a protective substrate 30 joined thereto with an adhesive agent 35. The protective substrate 30 has a manifold portion 32. The manifold portion 32 is at least part of the manifold 100. The manifold portion 32 in this embodiment is opened through the protective substrate 30 in the thickness direction (Z direction) and extends along the direction of the width of the pressure chambers 12 (+X direction). The manifold portion 32 communicates with the communicating space 15 of the substrate 10. These structural features make up the manifold 100, a common ink tank for the pressure chambers 12.

The protective substrate 30 also has a piezoelectric element housing 31 in a region including the piezoelectric elements 300. The piezoelectric element housing 31 has a space large enough not to interfere with the movement of the piezoelectric elements 300. This space may be sealed or not. The protective substrate 30 further has a through-hole 33 opened through the protective substrate 30 in the thickness direction (Z direction). Inside the through-hole 33, the ends of the lead electrodes 90 are exposed.

The protective substrate 30 can be made of, for example, Si, SOI, glass, a ceramic material, metal, or resin. A material that has substantially the same coefficient of thermal expansion as that of the substrate 10 is preferred. In this embodiment, the protective substrate 30 is made of Si, the same material as for the substrate 10.

On the protective substrate 30 is fastened a driver 120 that functions as a signal-processing unit. The driver 120 can be, for example, a circuit board or a semiconductor integrated circuit (IC). The driver 120 and the lead electrodes 90 are electrically coupled together by wiring 121, which is a set of bonding wires or any other kind of electroconductive wires run through the through-hole 33. The driver 120 can be electrically coupled to a printer controller 200 (see FIG. 1). Such a driver 120 functions as a control unit for the piezoelectric actuators (piezoelectric elements 300).

On the protective substrate 30 is a compliance substrate 40 joined thereto. The compliance substrate 40 is composed of a sealing film 41 and a stationary plate 42. The sealing film 41 is a film of a low-rigidity material, and the stationary plate 42 can be made of a hard material, such as metal. The region of the stationary plate 42 facing the manifold 100 is an opening 43 created by removing this portion of the plate all the way in the thickness direction (Z direction). One side (+Z side) of the manifold 100 is sealed with the flexible sealing film 41 alone.

Such a recording head 1 ejects ink droplets through the following operation. First, ink is taken from a not-illustrated external ink source via an ink inlet connected to the ink source, and the entire space from the manifold 100 to the nozzle openings 21 is filled with the ink. Then, in response to recording signals from the driver 120, voltage is applied across each of the first electrodes 60, which correspond one-to-one to the pressure chambers 12, and the second electrode 80, making the piezoelectric elements 300 flexurally deform. As a result, the pressure inside the pressure chambers 12 is increased, and ink droplets are ejected through the nozzle openings 21.

Piezoelectric Actuators

The following describes the structure of the piezoelectric elements 300 used as piezoelectric actuators in the recording head 1 with reference to a drawing.

Figure 5:
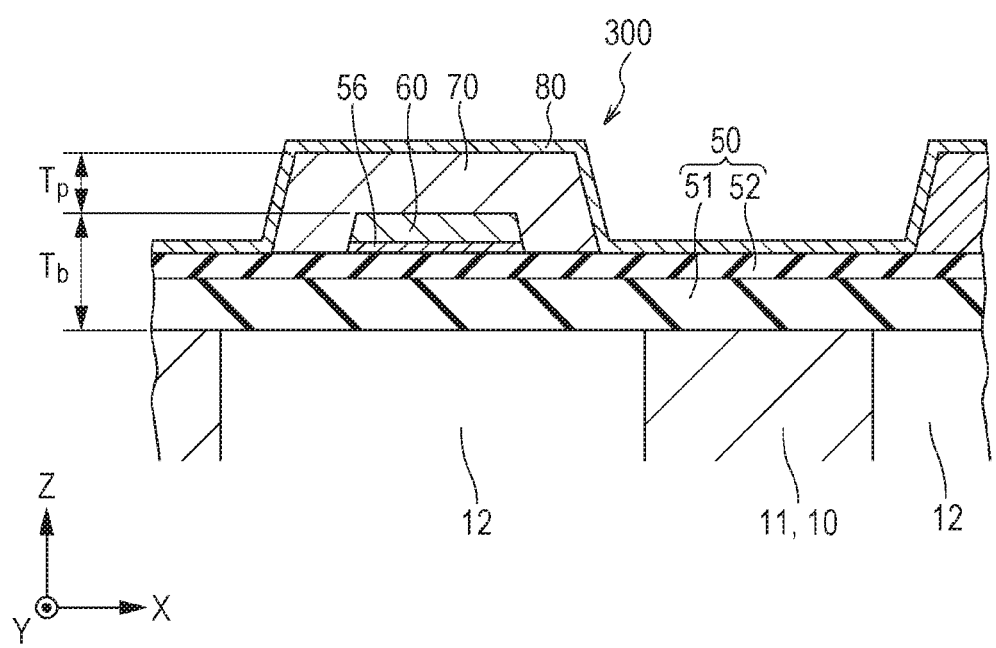
FIG. 5 is an enlarged cross-sectional diagram taken along line V-V of FIG. 4.

FIG. 5 is an enlarged cross-sectional diagram taken along line V-V of FIG. 4. As illustrated, a substrate 10 has pressure chambers 12 defined by multiple walls 11, and on this substrate 10 is a diaphragm 50 composed of an elastic film 51 and an insulating film 52. A contact layer 56, a first electrode 60, a piezoelectric layer 70, and a second electrode 80 stacked one after another on the diaphragm 50 form a moving portion of a piezoelectric element 300.

In this embodiment, the piezoelectric layer 70 is made of a composite oxide containing lead (Pb), zirconium (Zr), and Ti in the perovskite structure represented by the general formula $ABO_3$ ($ABO_3$ perovskite structure) (PZT composite oxide) so that the piezoelectric element 300 has electromechanical transduction capabilities and to ensure that a large displacement will be achieved. PZT composite oxides, superior in piezoelectric properties, are advantageous in improving characteristics. That is, the piezoelectric layer 70 contains a piezoelectric material that is a PZT composite oxide represented by formula (4):

$$Pb_x(Zr_y,Ti_{1-y})O_3 \qquad (4)$$

(where $1.14 \leq x \leq 1.22$ and $0.4 \leq y \leq 0.6$).

In formula (4), the A-site element Pb is in excess of the stoichiometric amount in $ABO_3$. Therefore $1.0 < x$, since x represents the total amount of Pb including the amount of Pb added in excess (Pb overage). When x=1.14, for example, the oxide contains 114 mol % Pb, assuming that the stoichiometric amount of Pb is 100 mol %. The Pb overage is therefore 14 mol %. When x=1.22, the oxide contains 122 mol % Pb, assuming that the stoichiometric amount of Pb is 100 mol %. The Pb overage is therefore 22 mol %. If the amount of A-site element Pb is not in excess or short of the stoichiometric amount, x=1.

In general, PZT is produced with Pb in excess of the stoichiometric amount. This aims to reduce lattice imperfections and is a countermeasure against the evaporation of Pb during the production process. It is well known that the excess of Pb exists at the B-site and becomes a p-type dopant. The amount of current that the PZT leaks is therefore proportional to the Pb overage, if no other factor contributes. Accordingly, it is preferred that the amount of Pb in the PZT composite oxide fall within the range of $1.14 \leq x \leq 1.22$. This improves the piezoelectric properties by reducing both lattice imperfections in and leakage from the PZT.

In other words, in formula (4), it is preferred that the molar ratio of the A-site (Pb) to the B-site (Zr+Ti) in the PZT composite oxide $(A/B)=(x/1)$ be 1.14 or more and 1.22 or less, more preferably 1.16 or more and 1.20 or less.

Moreover, in formula (4), it is preferred that the Zr content be 40 mol % or more and 60 mol % or less of the total amount of the B-site metal elements (in other words, the Ti content be 40 mol % or more and 60 mol % or less of the total amount of the B-site metal elements). That is, in formula (4), it is preferred that $0.4 \leq y \leq 0.6$. This gives the PZT composite oxide a composition advantageous for piezoelectric properties.

Then, an optimum overage of Pb is selected according to the lower-activation-energy range. This gives the piezoelectric layer in the piezoelectric element 300 high piezoelectric properties owing to fewer lattice imperfections. As detailed in the Examples section, it is preferred that in current-time curve (I-t curve) measurement (I-t measurement), the activation energy calculated from relaxation current using an Arrhenius plot be 0.6 [eV] or less, more preferably 0.5 [eV] or less. The relaxation current is the amount of current (current density [$\mu Acm^{-2}$]) at the time at which a downward trend in current turns upward.

The "lower-activation-energy range" refers to a range in which intentionally lowering the activation energy is effective in reducing the leakage level. Although the mechanism behind has yet to be made clear, there is a region in which the activation energy is specifically low (the mechanism of conduction is different) because of factors other than composition (e.g., firing temperature), presumably involving a conduction band other than that resulting from excessive Pb.

The piezoelectric material of which the piezoelectric layer 70 is made only needs to be a PZT composite oxide and is not limited to the compositions represented by formula (4). For example, another metal element (dopant) may be contained at the A-site and/or B-site of the lead zirconate titanate (PZT). Examples of such dopants include manganese (Mn), lithium (Li), barium (Ba), calcium (Ca), strontium (Sr), bismuth (Bi), tantalum (Ta), antimony (Sb), iron (Fe), cobalt (Co), silver (Ag), magnesium (Mg), zinc (Zn), and copper (Cu).

One or more such dopants may be contained. Typically, the dopant content is 20% or less, preferably 15% or less, more preferably 10% or less of the total amount of the elements that are contained as main constituents. Although the use of a dopant helps improvement in characteristics and the resulting diversification in structure and function, it is preferred that the PZT in the PZT composite oxide be present in an amount of more than 80%. This ensures that the PZT-derived characteristics will manifest themselves. If the PZT composite oxide contains such an additional element, too, it is preferred that the composite oxide have the $ABO_3$ perovskite structure.

The piezoelectric materials include materials that have a composition deficient in one or some of the elements, materials that have a composition that contains one or some of the elements excessively, and materials that have a composition in which one or some of the elements have been replaced with a different element. Unless the basic characteristics of the piezoelectric layer 70 are altered, any material that has a nonstoichiometric composition because of deficiency or excess or in which one or some of the elements have been replaced with a different element is also included in the piezoelectric materials according to this embodiment.

"Composite oxide containing Pb, Zr, and Ti in the $ABO_3$ perovskite structure" as mentioned herein is not limited to composite oxides containing Pb, Zr, and Ti in the $ABO_3$ perovskite structure. This means that this composite oxide includes piezoelectric materials described as mixed crystals that contain an $ABO_3$ perovskite composite oxide containing Pb, Zr, and Ti (e.g., an aforementioned exemplary PZT composite oxide) and another composite oxide having the $ABO_3$ perovskite structure.

The additional composite oxide can be of any kind. Examples include oxides such as those obtained by adding niobium, nickel, magnesium, and/or other metal elements to PZT, including lead titanate ($PbTiO_3$), lead zirconate ($PbZrO_3$), lead lanthanum titanate ($(Pb, La) TiO_3$), lead lanthanum zirconate titanate ($(Pb, La)(Zr, Ti)O_3$), and lead magnesium niobate zirconium titanate ($(Pb(Zr, Ti)(Mg, Nb)O_3$).

In the piezoelectric element 300, it is preferred that the thickness of the elastic film 51 be 0.1 μm or more and 2.0 μm or less, the thickness of the insulating film 52 be 0.01 μm or more and 1.0 μm or less, the thickness of the contact layer 56 be 0.005 μm or more and 0.1 μm or less, the thickness of the first electrode 60 be 0.01 μm or more and 1.0 μm or less, the thickness of the piezoelectric layer 70 be 0.1 μm or more and 5.0 μm or less, and the thickness of the second electrode 80 be 0.01 μm or more and 1.0 μm or less. If a seed layer is formed, the thickness of the seed layer is 0.08 μm or less, preferably 0.01 μm or more and 0.05 μm or less. These thicknesses of the elements are merely an example and can be changed unless the gist of the aspect of the invention is altered.

Incidentally, the piezoelectric strain in a piezoelectric element 300 perpendicular to the direction in which the electric field is applied (transverse piezoelectric strain) $S_{31}$ is represented by formula (5), where V is the voltage applied, $d_{31}$ is the piezoelectric constant, L is the length (in the X direction) of the piezoelectric element 300, and d is the thickness (in the Z direction) of the piezoelectric element 300.

$$S_{31}=d_{31}\times(L/d)\times V \qquad (5)$$

From formula (5), it can be seen that thinning the piezoelectric layer 70 in a piezoelectric element 300 leads to an improvement in transverse piezoelectric strain $S_{31}$. However, as described hereinafter, the piezoelectric layer 70 is a stack of multiple piezoelectric films 74 (see FIG. 8 and other drawings), and its thickness is 0.1 μm or more and 5.0 μm or less. Since the thickness of the piezoelectric layer 70 and the thickness of the diaphragm 50 in the piezoelectric element 300 are comparable, thinning the piezoelectric layer 70 affects the force for deforming the diaphragm 50, resulting in a decrease in the displacement of the piezoelectric element 300 as a whole. That is, thinning the piezoelectric layer 70 in a piezoelectric element 300 increases the transverse piezoelectric strain $S_{31}$ and reduces the force, whereas thickening the piezoelectric layer 70 reduces the transverse piezoelectric strain $S_{31}$ and improves the force. The improvement of the piezoelectric properties of the piezoelectric element 300 as a whole therefore depends crucially on the balance between these two parameters. Moreover, if the thickness of the piezoelectric layer 70 is greater than the thickness of the diaphragm 50, the center of stress comes to a position disadvantageous for vibration. In this case, too, the displacement of the piezoelectric element 300 as a whole is reduced, affecting the vibration properties.

As a solution, in this embodiment, it is preferred in the piezoelectric element 300 that when the thickness of the piezoelectric layer 70 is $T_p$ and the total thickness of the diaphragm 50 and first electrode 60 is $T_b$, the $T_p$-to-$T_b$ relationship $(T_p/T_b)$ satisfy $0.47<T_p/T_b<1.33$, more preferably $0.51<T_p/T_b<1.15$. A $T_p/T_b$ ratio deviating from a predetermined range leads to a decrease in electromechanical coupling coefficient (described hereinafter). If one of the elastic film 51 and the insulating film 52 is omitted, $T_b$ is the total thickness of the other and the first electrode 60. If the first electrode 60 is provided directly on the substrate 10, $T_b$ is the thickness of the first electrode 60.

The force for deforming the diaphragm 50 is proportional to the product of the elastic modulus and deformation of the piezoelectric layer 70, which is the pressure generator. The elastic modulus is determined by the structure of the piezoelectric actuator, and the deformation is determined by the efficiency of the conversion from input electric energy into mechanical energy, or by the electromechanical coupling coefficient. When the elastic modulus can be deemed to be constant, the actuator performance can be assessed on the basis of the magnitude of the electromechanical coupling coefficient.

As detailed in the Examples section, the electromechanical coupling coefficient k has the relationship of formula (6), where $f_r$ is the frequency at which the impedance bottoms out and $f_a$ is the frequency at which the impedance peaks.

$$k^2=(f_a^2-f_r^2)/(f_a^2) \qquad (6)$$

It is preferred that the electromechanical coupling coefficient k be 0.278 or more, more preferably 0.284 or more. These give a piezoelectric element 300 that has a piezoelectric layer 70 that achieves higher piezoelectric properties by virtue of improved piezoelectric properties attained by thinning the piezoelectric layer 70 combined with controlled loss of the force for deforming the diaphragm 50.

The piezoelectric layer 70 is a stack of multiple piezoelectric films 74 (see FIG. 8 and other drawings), and the piezoelectric films 74 each contain Pb, Zr, and Ti. That is, the piezoelectric films 74 are PZT films made of an aforementioned PZT composite oxide, specifically films formed of PZT crystals grown with a predetermined preferred orientation (crystallized from precursor solutions for the PZT composite oxide by removing solvent and other unnecessary components and heating the residue). In this embodiment, it is preferred to use a piezoelectric layer 70 in which the crystals of the piezoelectric material have preferred (100) orientation.

A piezoelectric layer 70 formed by piezoelectric films 74 (PZT films) with preferred (100) orientation, in this embodiment, refers to one in which the PZT crystals have preferred (100) orientation. The piezoelectric layer may have, for example, preferred (110) or (111) orientation, depending on factors such as the piezoelectric material for the optional seed layer and the production process. A piezoelectric layer 70 with preferred (100) orientation is easy to improve in terms of characteristics, compared with a piezoelectric layer having random orientation or a preferred orientation other than (100).

Preferred orientation as mentioned herein is defined as a state in which 50% or more, preferably 80% or more, of the crystals have a predetermined orientation. For example, "with preferred (100) orientation" includes the case in which all crystals in the piezoelectric layer 70 are (100)-oriented and cases in which a half or more (50% or more, preferably 80% or more) of the crystals are (100)-oriented.

The material for the first electrode 60 and that for the second electrode 80 only need to be a material that is not oxidized and remains electroconductive during the formation of the piezoelectric element 300. Examples of such materials include metallic materials such as platinum (Pt), iridium (Ir), gold (Au), aluminum (Al), copper (Cu), Ti, silver (Ag), palladium (Pd), nickel (Ni), and stainless steel; tin-oxide electroconductive materials such as indium tin oxide (ITO) and fluorine-doped tin oxide (FTC)), zinc-oxide electroconductive materials such as gallium-doped zinc oxide (GZO), and oxide electroconductive materials such as iridium oxides ($IrO_X$), strontium ruthenate ($SrRuO_3$), lanthanum nickelate ($LaNiO_3$), and element-doped strontium titanates; and electroconductive polymers. One of these materials can be used alone as an electrode material, or alternatively a stack of layers of multiple materials may be used. The electrode material for the first electrode 60 and the electrode material for the second electrode 80 can be the same or different.

Method for Producing Piezoelectric Elements

The following describes an example of a method for producing piezoelectric elements 300 and a method for producing recording heads 1 with reference to drawings. FIGS. 6 to 12 are cross-sectional diagrams for describing an example of the production of ink jet recording heads.

Figure 6:
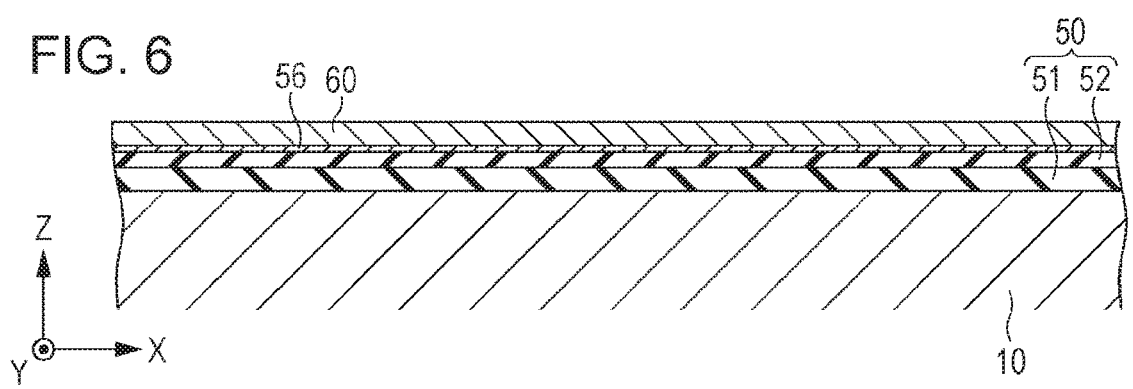
FIG. 6 is a cross-sectional diagram for describing an example of the production of ink jet recording heads.

First, as illustrated in FIG. 6, a Si single-crystal substrate is prepared as a substrate 10. Then, a $SiO_2$ elastic film 51 is formed on the surface of the substrate 10 by thermally oxidizing the substrate 10. A zirconium film is then formed on the elastic film 51, for example by sputtering or vapor deposition, and this film is thermally oxidized to give a $ZrO_2$ insulating film 52. In this way, a diaphragm 50 composed of an elastic film 51 and an insulating film 52 is formed on the substrate 10. Then, a $TiO_X$ contact layer 56 is formed on the insulating film 52. The contact layer 56 can be formed by, for example, sputtering or thermal oxidation of a Ti film. Then, a Pt first electrode 60 is formed on the contact layer 56. The method for forming the first electrode 60 can be selected as appropriate according to the electrode material and can be, for example, a gas-phase film formation process, such as sputtering, vacuum deposition (PVD), or laser ablation, or a liquid-phase film formation process, such as spin coating.

Figure 7:
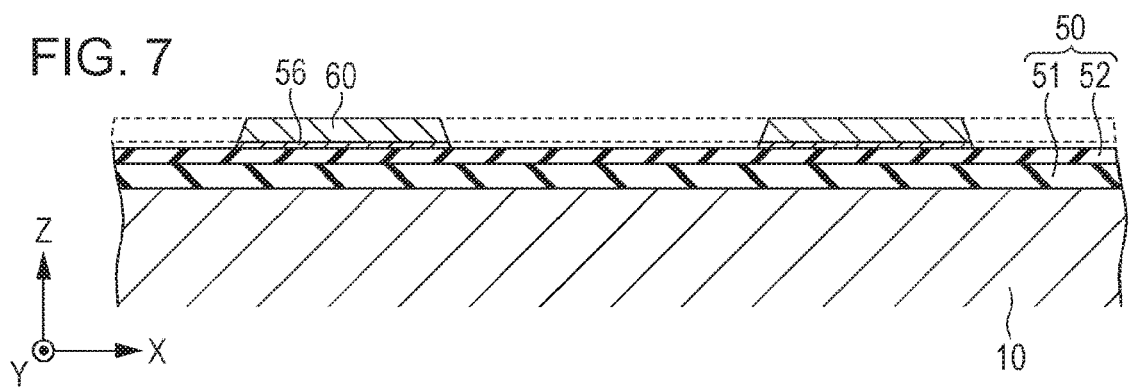
FIG. 7 is a cross-sectional diagram for describing an example of the production of ink jet recording heads.

Then, as illustrated in FIG. 7, resist in a predetermined shape (not illustrated) is formed as a mask on the first electrode 60, and the contact layer 56 and first electrode 60 are patterned simultaneously. The patterning of the contact layer 56 and first electrode 60 can be done by, for example, a dry etching process, such as reactive ion etching (RIE) or ion milling, or by wet etching, an etching process in which an etchant is used. The shape of the patterned contact layer 56 and first electrodes 60 is not critical.

Figure 8:
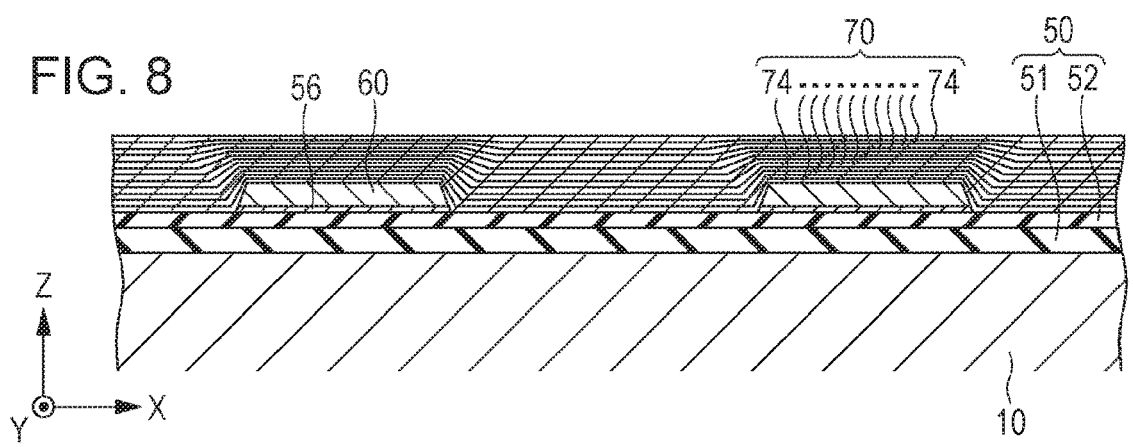
FIG. 8 is a cross-sectional diagram for describing an example of the production of ink jet recording heads.

Then, as illustrated in FIG. 8, multiple piezoelectric films 74 are formed on the first electrodes 60. The piezoelectric layer 70 is formed by multiple piezoelectric films 74. The piezoelectric layer 70 can be formed by, for example, chemical solution deposition (wet deposition), in which solutions containing a metal complex (precursor solutions) are applied, the applied coating is dried, and the dried coating is fired at high temperatures to give a metal oxide. Alternatively, the piezoelectric layer 70 may be formed by, for example, laser ablation, sputtering, pulsed laser deposition (PLD), CVD (chemical vapor deposition), or aerosol deposition. In this embodiment, wet deposition (liquid-phase deposition) is used to obtain a (100)-oriented piezoelectric layer 70.

Wet deposition (liquid-phase deposition) is a technique in which a film is formed by a chemical solution deposition process, such as MOD or the sol-gel process, and is a concept distinct from gas-phase deposition, such as sputtering. In this embodiment, a gas-phase deposition process may be used as long as a (100)-oriented piezoelectric layer 70 can be formed.

A piezoelectric layer 70 formed by wet deposition (liquid-phase deposition), for example, has multiple piezoelectric films 74 each formed by a series of operations that are applying precursor solutions to form a precursor film (application), drying the precursor film (drying), degreasing the dried precursor film by heating (degreasing), and firing the degreased precursor film (firing). That is, the piezoelectric layer 70 is formed by repeating a series of operations from application to firing. In this series of operations, the firing may be carried out after repeated cycles of application through degreasing.

A layer or film formed by wet deposition has an interface. A layer or film formed by wet deposition has traces of application or firing left therein, and such traces form an interface whose presence can be confirmed by observing a cross-section of the layer or film or analyzing the distribution of element concentrations in the layer (or in the film). Strictly speaking, an interface means a boundary between layers or films, but here it means the vicinity of an edge of a layer or film. When a cross-section of a layer or film formed by wet deposition is observed, for example by an electronic microscope, such an interface is seen near the boundary with the next layer or film as a portion in a color darker or lighter than the color of the rest. When the distribution of element concentrations is analyzed, such an interface is found near the boundary with the next layer or film as a portion with element concentrations higher or lower than in the rest. Formed by repeating a series of operations from application to firing or by performing firing after repeated cycles of application through degreasing (composed of multiple piezoelectric films 74), the piezoelectric layer 70 has multiple interfaces corresponding to the piezoelectric films 74.

The following is an example of an actual procedure for the formation of the piezoelectric layer 70 by wet deposition. First, precursor solutions, including an MOD solution and a sol each containing a metal complex, for the formation of the piezoelectric layer 70 are prepared individually (preparation). Then, the precursor solutions for the piezoelectric layer 70 are applied to the patterned first electrodes 60, for example by spin coating, to form a precursor film (application). Then, this precursor film is heated to a predetermined temperature, for example between 130° C. and 250° C., and dried for a certain period of time (drying), and the dried precursor film is degreased by heating it to a predetermined temperature, for example between 300° C. and 450° C., and holding for a certain period of time (degreasing). The degreased precursor film is heated to a higher temperature, for example a temperature between 500° C. and 800° C., and held at that temperature for a certain period of time to be crystallized and form a piezoelectric film 74 (firing). After the formation of this piezoelectric film 74, the application, drying, degreasing, and firing are repeated, forming a piezoelectric layer 70 composed of multiple piezoelectric films 74.

Each of the precursor solutions is a solution or dispersion, in an organic solvent, of one of metal complexes that can form a PZT composite oxide when fired. That is, the precursor solutions for the piezoelectric layer 70 contain predetermined elements (in this embodiment, Pb, Zr, and Ti) as the central metal of the metal complex. The precursor solutions for the piezoelectric layer 70 may be mixed with a metal complex that contains an element other than the predetermined elements.

Each metal complex containing a predetermined element can be, for example, an alkoxide, organic acid salt, or β-diketone complex. As for the proportions of the metal complexes in the precursor solutions, the metal complexes can be mixed in such proportions that the predetermined elements in the PZT composite oxide will be present in the desired molar ratio.

An example of a Pb-containing metal complex is lead acetate. Examples of Zr-containing metal complexes include tetra-n-propoxy zirconium, zirconium acetylacetonate, monoacetylacetonate, and zirconium bisacetylacetonate. Examples of Ti-containing metal complexes include titanium alkoxides, such as titanium tetraisopropoxide, titanium 2-ethylhexanoate, and titanium acetate. A combination of two or more metal complexes can also be used. For example, as Zr-containing metal complexes, zirconium acetylacetonate and zirconium tetraacetylacetonate can be used in combination.

Organic solvents used in the preparation of the precursor solutions include, for example, propanol, butanol, pentanol, hexanol, octanol, ethylene glycol, propylene glycol, octane, decane, cyclohexane, xylene, toluene, tetrahydrofuran, acetic acid, octylic acid, 2-n-butoxyethanol, n-octane, and mixtures thereof.

The precursor solutions may contain an additive that stabilizes the dispersion of the metal complex. Examples of such additives include 2-ethylhexanoic acid and ethanolamine.

The heater used in the drying, degreasing, and firing can be, for example, an RTA (rapid thermal annealing) system, which provides heating through irradiation with an infrared lamp, or a hot plate.

Figure 9:
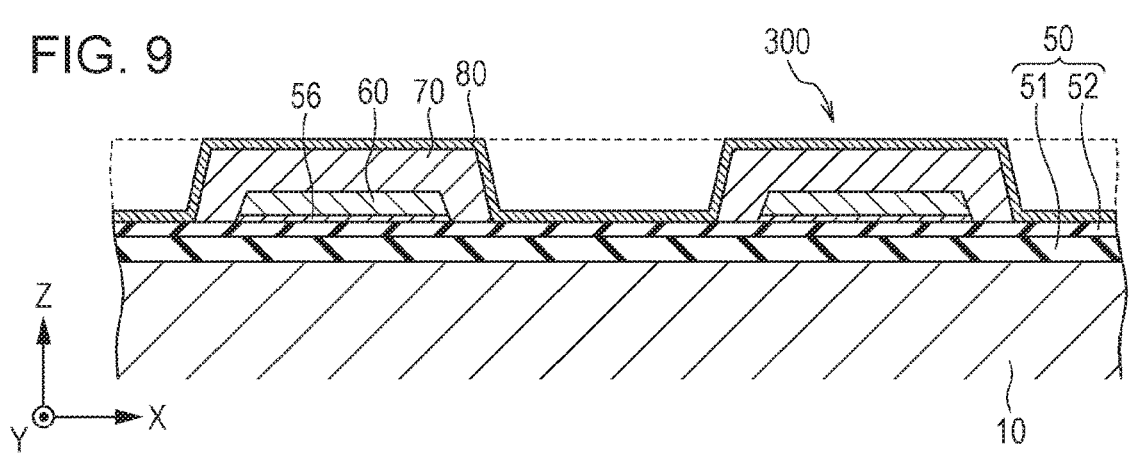
FIG. 9 is a cross-sectional diagram for describing an example of the production of ink jet recording heads.

Then, as illustrated in FIG. 9, the piezoelectric layer 70 is patterned. The patterning can be done by a dry etching process, such as reactive ion etching or ion milling, or by wet etching, an etching process in which an etchant is used. The shape of the patterned piezoelectric layers 70 is not critical. Then, a second electrode 80 is formed on the patterned piezoelectric layers 70. The methods that can be used to form the second electrode 80 are the same as those for the first electrode 60.

Before or after the formation of the second electrode 80 on the piezoelectric layers 70, reheating (post-annealing) may optionally be performed in the temperature range of 600° C. to 800° C. Such a post-annealing forms good interfaces between the contact layer 56 and the first electrodes 60, between the first electrodes 60 and the piezoelectric layers 70, and between the piezoelectric layers 70 and the second electrode 80 and improves the crystallinity of the piezoelectric layers 70.

Figure 10:
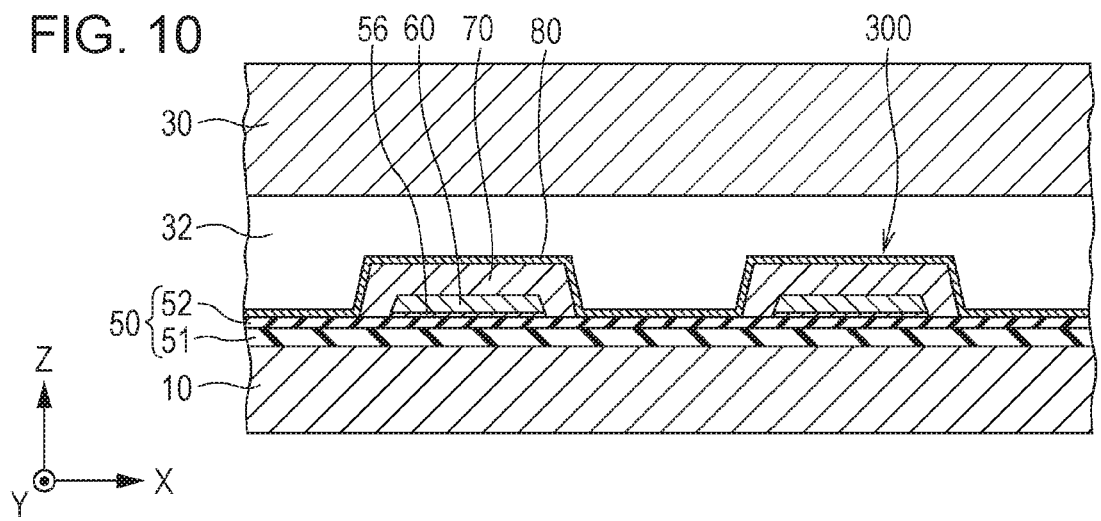
FIG. 10 is a cross-sectional diagram for describing an example of the production of ink jet recording heads.

Then, as illustrated in FIG. 10, a protective substrate 30 as a protective substrate wafer is joined to the piezoelectric element 300 side of the substrate 10 with an adhesive agent 35 (see FIG. 4). After that, the surface of the protective substrate 30 is ground to make this substrate thinner, and a manifold portion 32 and a through-hole 33 (see FIG. 4) are created through the protective substrate 30.

Figure 11:
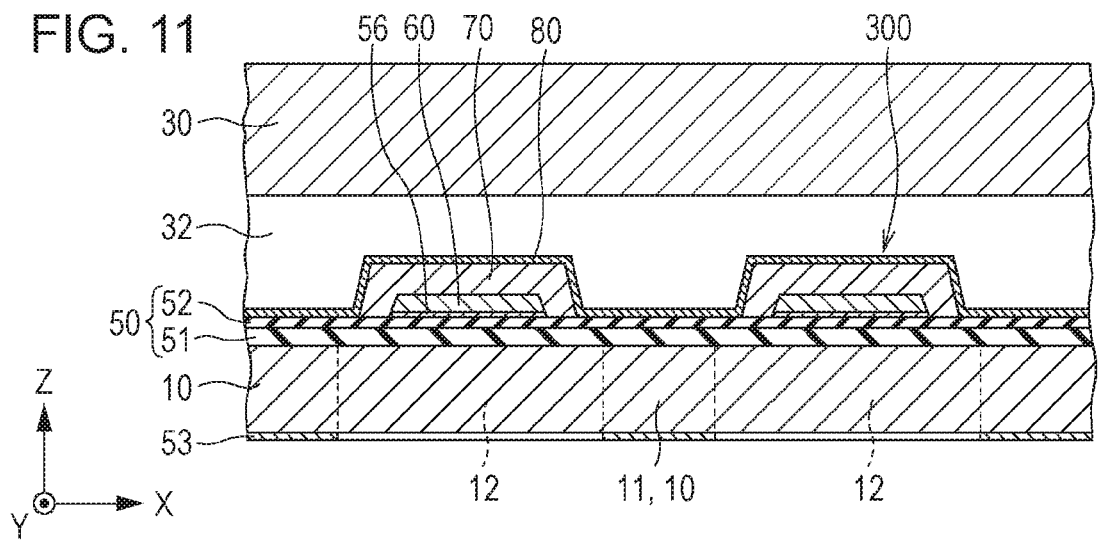
FIG. 11 is a cross-sectional diagram for describing an example of the production of ink jet recording heads.
Figure 12:
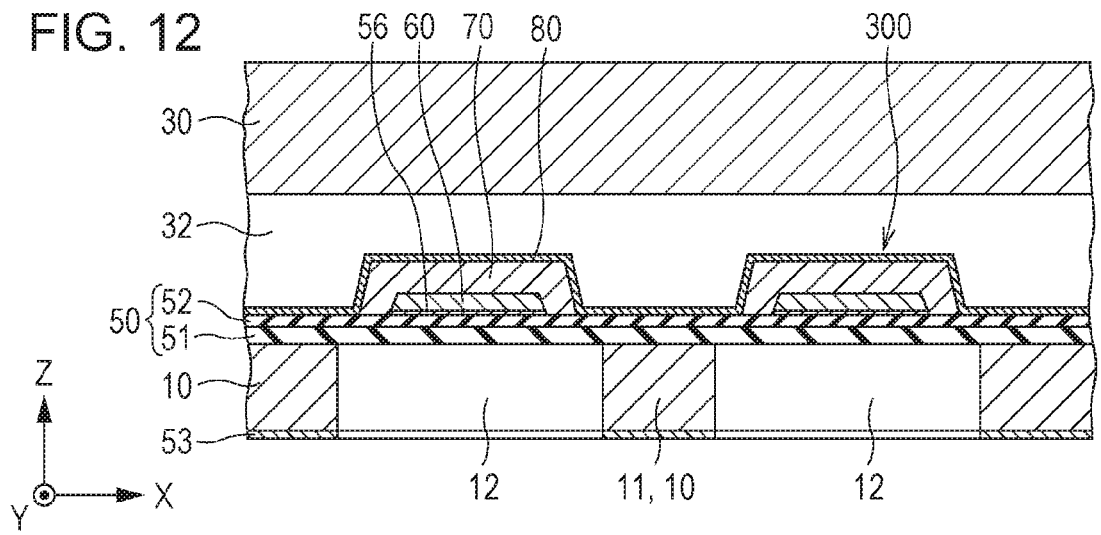
FIG. 12 is a cross-sectional diagram for describing an example of the production of ink jet recording heads.

Then, as illustrated in FIG. 11, a mask coating 53 is formed on the surface of the substrate 10 opposite the piezoelectric elements 300 and patterned into a predetermined shape. Then, as illustrated in FIG. 12, the substrate 10 is anisotropically etched using an alkali solution, such as a KOH solution (wet etching), with the mask coating 53 thereon, dividing the substrate 10 by multiple walls 11 and creating pressure chambers 12. After that, besides the pressure chambers 12, each corresponding to one of the piezoelectric elements 300, ink supply paths 13, communicating paths 14, and a communicating space 15 (see FIG. 4) are created.

Then, the margins of the substrate 10 and protective substrate 30 are cut away, for example by dicing. A nozzle plate 20 (see FIG. 4) is then joined to the surface of the substrate 10 opposite the piezoelectric elements 300, and a compliance substrate 40 (see FIG. 4) is joined to the protective substrate 30. Through the process up to this point, an array of chips of recording heads 1 (FIG. 4) is completed. This array is divided into individual chips. In this way, recording heads 1 are obtained.

Embodiment 2

Ultrasonic Device

The following describes, with reference to drawings, an ultrasonic probe as an example of an ultrasonic device that includes an ultrasonic sensor according to Embodiment 2 of an aspect of the invention.

Figure 13:
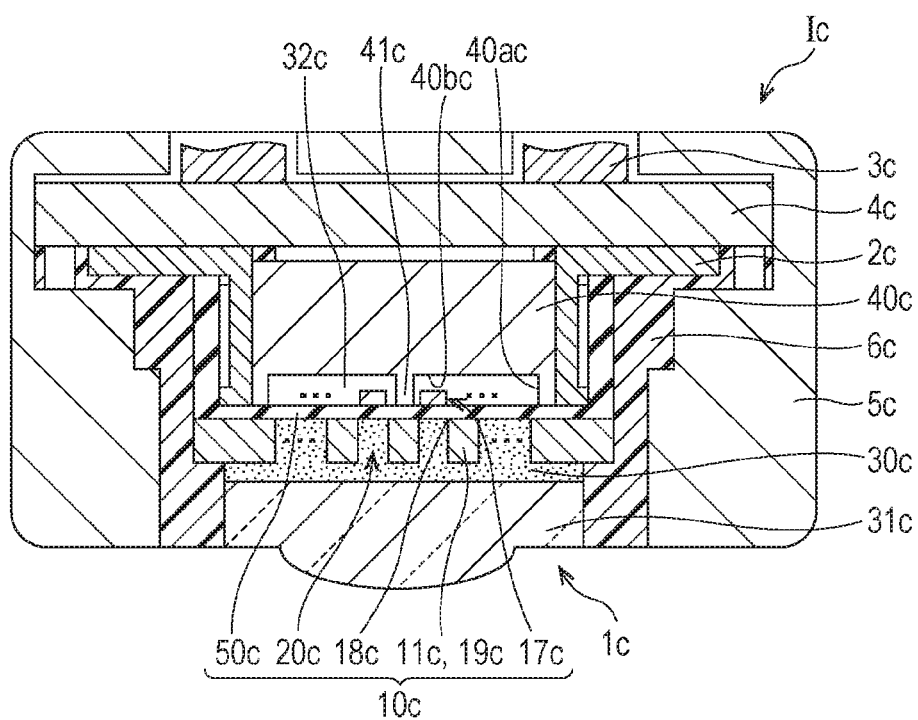
FIG. 13 is a cross-sectional diagram that illustrates an example of the structure of an ultrasonic probe.

FIG. 13 is a cross-sectional diagram that illustrates an example of the structure of an ultrasonic probe. As illustrated, the ultrasonic probe (probe) Ic includes an ultrasonic sensor 1c of CAV surface type, a flexible printed circuit board (FPC board 2c) coupled to the ultrasonic sensor 1c, a cable 3c coming from a not-illustrated device terminal, an intermediate substrate 4c that mediates between the FPC board 2c and the cable 3c, an enclosure 5c that protects the ultrasonic sensor 1c, FPC board 2c, and coupling substrate 4c, and waterproof resin 6c packed between the enclosure 5c and the ultrasonic sensor 1c. As detailed hereinafter, the ultrasonic sensor 1c includes an acoustic matching layer 30c that propagates ultrasonic waves resulting from the drive of an ultrasonic element 10c, a lens component 31c as a diffractor that diffracts the ultrasonic waves, and a cover plate 40c. Note that the probe Ic is not limited to this structure and may optionally have other components.

The ultrasonic sensor 1c, fitted in the probe Ic, has both transmitter and receiver functions. This ultrasonic sensor 1c is configured such that transmission ultrasonic waves are sent out through the acoustic matching layer 30c and lens component 31c according to the rate of repeated transmission of the ultrasonic sensor 1c. While the transmission ultrasonic waves are sent out at predetermined intervals, reflection ultrasonic waves, reflected off the subject of measurement, are received passing through the acoustic matching layer 30c and lens component 31c. Based on the waveform signals of these transmission ultrasonic waves and reflection ultrasonic waves, the information about the subject of measurement (position, shape, etc.) is detected at the device terminal of the probe Ic.

Such an ultrasonic sensor 1c offers reduced variability in transmission and reception sensitivity and improved reception sensitivity. The use of the ultrasonic sensor 1c in a probe Ic therefore gives the probe Ic superior detection sensitivity. The ultrasonic sensor 1c does not need to be of transceiver type but can also be applied to, for example, the transmission-only or reception-only type. The type of the ultrasonic sensor 1c is not critical to the structure of the probe Ic.

Moreover, the ultrasonic sensor 1c does not need to be of the type in which the region through which ultrasonic waves pass is on the side of the diaphragm 50c opposite the piezoelectric elements 17c (CAV surface type) but can also be applied to the type in which the region through which ultrasonic waves pass is on the piezoelectric element 17c side of the diaphragm 50c (ACT surface type). In an ultrasonic sensor 1c of CAV surface type, as compared with an ultrasonic sensor of ACT surface type, the piezoelectric elements 17c, a component of the ultrasonic element 10c, are distant from the subject of measurement. This structure is therefore highly repellent against moisture coming from the outside and reaching the piezoelectric elements 17c and, as a result, gives the ultrasonic sensor 1c superior electrical safety during use. When the piezoelectric elements 17c are thin films, furthermore, the use of the CAV surface structure leads to improved handling during production and, therefore, helps in handling the ultrasonic sensor 1c.

Ultrasonic Sensor

Figure 14:
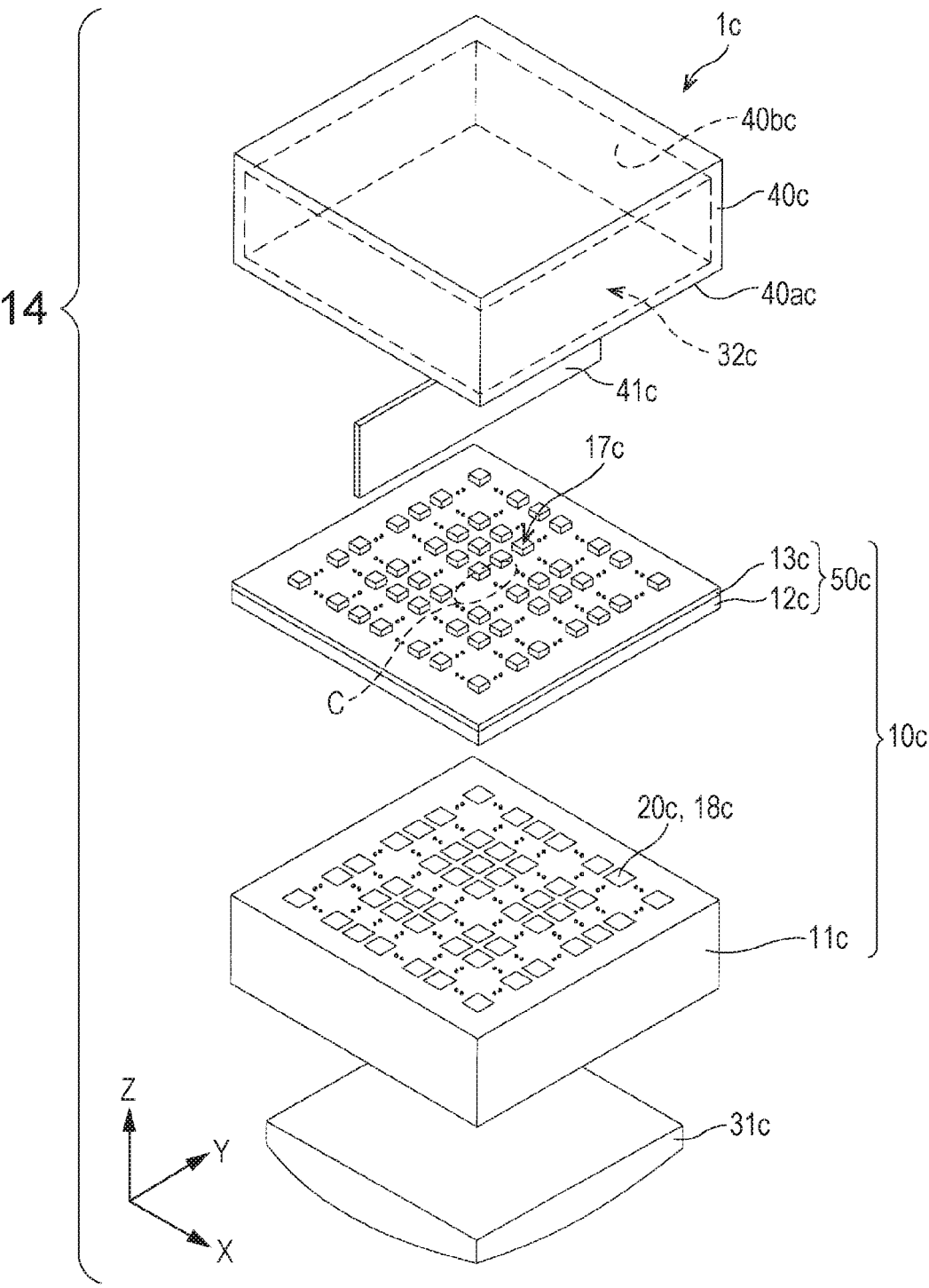
FIG. 14 is an exploded perspective diagram that illustrates an example of the structure of an ultrasonic sensor.

FIG. 14 is an exploded perspective view of an ultrasonic sensor. As illustrated in FIGS. 13 and 14, the ultrasonic sensor 1c includes an ultrasonic element 10c, an acoustic matching layer 30c, a lens component 31c, and a cover plate 40c. In FIG. 14, the cover plate 40c and support 41c are depicted as if they are separate components, but actually, these two elements are integral as illustrated in FIG. 13. Note that the ultrasonic sensor 1c is not limited to this structure and may optionally have other components.

Since the ultrasonic sensor 1c is of CAV surface type, the acoustic matching layer 30c is disposed in cavities 20c. A resin or other material capable of acoustic matching is packed, for example in the cavities 20c in the substrate 11c, to form an acoustic matching layer 30c. This prevents a rapid change in acoustic impedance between the ultrasonic element 10c and the subject of measurement, thereby preventing the associated decrease in the efficiency of ultrasonic propagation. Examples of materials that can be used for such an acoustic matching layer 30c include silicone materials, such as silicone oil, silicone resin, and silicone rubber, and other materials having fluidity (fluidic materials). However, the materials that can be used for the acoustic matching layer 30c are not limited to these examples, and the manufacturer can use a material selected as appropriate according to factors such as the purpose of use of the ultrasonic sensor 1c.

The lens component 31c is disposed on the side of the substrate 11c opposite the diaphragm 50c. The lens component 31c focuses the ultrasonic waves. If, for example, the ultrasonic waves are focused by electronic focusing, the lens component 31c can be omitted. Moreover, the lens component 31c can be replaced with, for example, a protective plate that does not function to focus ultrasonic waves. In this embodiment, the acoustic matching layer 30c also functions to join or bond the lens component 31c and the substrate 11c together. The acoustic matching layer 30c is interposed between the lens component 31c and the substrate 11c, forming the ultrasonic sensor 1c. Examples of materials that can be used for the lens component 31c are the same as those for the acoustic matching layer 30c, such as silicone materials. However, the materials that can be used for the lens component 31c are not limited to these examples, and the manufacturer can use a material selected as appropriate according to factors such as the purpose of use of the ultrasonic sensor 1c. The use of a material similar to that for the acoustic matching layer 30c helps in joining or bonding the acoustic matching layer 30c and the lens component 31c together.

The cover plate 40c is disposed on the insulating film 13c side of the diaphragm 50c. In the middle of the cover plate 40c is a recess (piezoelectric element housing 32c), and this piezoelectric element housing 32c is surrounded by the edge 40ac and surface 40bc of the cover plate 40c. The piezoelectric element housing 32c covers the surroundings of the ultrasonic element 10c (a region including the top and sides of the ultrasonic element 10c). Therefore, the top of the ultrasonic element 10c is covered with the surface 40bc of the cover plate 40c, and the sides with the edge 40ac.

The thickness, in the Z direction, of the piezoelectric element housing 32c is, but is not limited to, 80 µm. The piezoelectric element housing 32c may have any thickness, in the Z direction, that allows a space large enough not to interfere with the drive of the ultrasonic element 10c. The piezoelectric element housing 32c may be filled with atmospheric air or air (dry air) or with resin. Alternatively, the piezoelectric element housing 32c may be filled with a filler gas species, such as nitrogen ($N_2$) or argon (Ar). The selection of the filler gas species and pressure is at the manufacturer's discretion.

The cover plate 40c has been bonded or joined to the diaphragm 50c at its edge 40ac and with a support 41c, described hereinafter, therebetween. The method for bonding or joining the cover plate 40c can be, for example, but is not limited to, the use of an adhesive agent. The thickness, in the Z direction, of the cover plate 40c is, but is not limited to, 400 µm.

The ultrasonic sensor 1c has a support 41c between the surface 40bc of the cover plate 40c and the insulating film 13c of the diaphragm 50c at a position where the support 41c does not overlap the piezoelectric elements 17c. This support 41c supports the diaphragm 50c. Thus, the lens component 31c may be pressed toward the acoustic matching layer 30c side, for example to mount the lens component 31c onto the ultrasonic element 10c or to ensure the adhesion between the ultrasonic element 10c and the lens component 31c. Even without the lens component 31c or with a different element instead of the lens component 31c, there is still a possibility that compressive force may be applied to the diaphragm 50c from the acoustic matching layer 30c side to ensure adhesion between the elements. The ultrasonic sensor 1c remains highly reliable even if a predetermined external pressure is applied to the diaphragm 50c in a way described above, because the support 41c limits the occurrence of structural strain.

Moreover, since the support 41c is positioned between the piezoelectric elements 17c so as not to overlap the piezoelectric elements 17c, the piezoelectric elements 17c are not excessively restrained by the support 41c. The efficiency of the transmission and that of the reception of ultrasonic waves are therefore not excessively reduced compared with those without the support 41c. The support 41c has been bonded or joined to the ultrasonic element 10c side with, for example, an adhesive agent, but this is not the only possible bonding or joining method.

The support 41c has the shape of a beam that extends along the Y direction. This allows the support 41c supports the diaphragm 50c in a wide range in the Y direction. The beam-shaped support 41c may extend along the X direction rather than the Y direction. One extending end of the beam-shaped support 41c may be apart from the edge 40ac of the cover plate 40c. As long as at least one of its ends in the direction in which it extends is in contact with the edge 40ac of the cover plate 40c, the support is included in the beam-shaped support 41c according to an aspect of the invention.

Naturally, the support 41c does not need to be in the shape of a beam. The support 41c does not need to be linear in the direction in which it extends. Although some methods for the production of the support 41c may give the support 41c a form in which its cross-sectional area in the XY plane varies in the Z direction, such a form is included in the support 41c according to an aspect of the invention as long as the diaphragm 50c can be supported.

The middle of the piezoelectric element housing 32c is relatively distant from the edge 40ac of the cover plate 40c. Without the support 41c, therefore, the diaphragm 50c would often have low rigidity at the center C, which corresponds to the middle of the piezoelectric element housing 32c. Thus, the support 41c is positioned in the middle of the piezoelectric element housing 32c to support such a center C of the diaphragm 50c.

In the ultrasonic sensor 1c, the number, arrangement, shape, etc., of supports 41c is at the manufacturer's discretion. For example, there may be multiple supports 41c. In this case, it is preferred that the supports 41c be equally spaced in the piezoelectric element housing 32c. This ensures that the diaphragm 50c is supported uniformly. It is therefore preferred that the number of supports 17c be three or a larger odd number. This is because when the supports 41c are equally spaced in the piezoelectric element housing 32c, the middle support 41c can come near the center C of the diaphragm 50c. About three supports 41c, for example, would be neither too many nor too few. Naturally, it is acceptable to provide the support(s) 41c only off the center C of the diaphragm 50c.

The beam-shaped support 41c is formed by wet-etching the cover plate 40c. As such, the support 41c is formed without altering the material of which the cover plate 40c is made, and has the same composition as the cover plate 40c. Wet etching, weak in working accuracy but quick to remove a large area, for example compared with dry etching, is a suitable method for the production of the beam-shaped support 41c.

The substrate 11c has multiple walls 19c. These multiple walls 19c define multiple cavities (CAV) (hereinafter referred to as cavities 20c) along the X and Y directions. The cavities 20c are created through the substrate 11c in the thickness direction (Z direction). That is, the substrate 11c has openings 18c on the diaphragm 50c side thereof. The openings 18c are arranged in a two-dimensional pattern: multiple openings 18c in the X direction and in the Y direction. Many variations are possible in the arrangement and shape of the openings 18c. For example, there may be a one-dimensional chain of openings 18c: multiple openings 18c along one of the X and Y directions. The openings 18c may be square (the X-to-Y length ratio is 1:1) or rectangular (the X-to-Y length ratio is not 1:1) when the piezoelectric elements 17c are viewed from right above (in the Z direction).

The ultrasonic element 10c may have the same structure as a piezoelectric element 300 according to Embodiment 1, but may optionally have other components. The details of a component of the ultrasonic element may be left out if the component has an equivalent in the piezoelectric element 300.

In general, an ultrasonic sensor has ultrasonic elements in a two-dimensional pattern, in which the ultrasonic elements are lined up in an X direction and a Y direction, which is perpendicular to the X direction. The X direction is defined as the scan direction, and the Y direction as the slice direction. In the exemplary structure in this embodiment, 16 ultrasonic elements 10c are lined up in the Y direction, or the slice direction, and 64 ultrasonic elements 10c in the X direction, or the scan direction, although FIG. 14 illustrates only some of them in each direction. While such an ultrasonic sensor 1c is scanned in the scan direction (X direction), each row of ultrasonic elements 10c in the slice direction (Y direction) is driven, or transmits and receives ultrasonic waves. In this way, sensing information in the slice direction is acquired continuously in the scan direction.

Examples of materials that can be used for the cover plate 40c, support 41c, and individual components of the ultrasound element 10c are the same as those for the protective substrate 30 and individual components of the piezoelectric elements 300 in Embodiment 1.

Examples

The following describes an aspect of the invention in more detail by providing examples. No aspect of the invention is limited to these examples.

Fabrication of Sample 1

First, a Si single-crystal substrate (substrate 10) with a diameter of 149 mm and a thickness of 625 μm was thermally oxidized in a stream of oxygen in a furnace at 1100° C. for 22 hours to form a 0.5-μm SiO$_2$ film (elastic film 51) on the surface of the substrate 10. Then, Ti (20-nm thick), Ir (20-nm thick), Pt (60-nm thick), and Ir (20-nm thick) layers were formed one after another on the elastic film 51 to form a first electrode 60.

Then, an aqueous solution of acetic acid as the main solvent was mixed with titanium tetra-i-propoxide and zirconium tetra-n-butoxide, and the mixture was stirred with lead acetate. The resulting mixture was heated with polyethylene glycol at 90° C. for 2 hours. The heated mixture was allowed to cool to room temperature, giving a precursor solution. This precursor solution was prepared so that the proportions of the individual elements in the resulting PZT layer (piezoelectric layer 70), a layer of a PZT composite oxide and described below, would satisfy formula (7).

$$Pb_x(Zr_y,Ti_{1-y})O_3 \quad (7)$$

(where x=1.14 and 0.4≤y≤0.6)

Then, the prepared precursor solution was applied by spin coating to the substrate 10, with the first electrode 60 thereon, in such a manner that the thickness of the piezoelectric layer 70 would fall within the range of 0.1 μm to 0.15 μm (application). This layer was dried at 180° C. (drying) and then degreased at 400° C. (degreasing). After three repeated cycles of application through degreasing, annealing was performed at 750° C. in an oxygen atmosphere using an RTA system (firing), producing a PZT film (piezoelectric film 74).

Such a series of operations from application to firing was repeated to form multiple piezoelectric films 74. In this way, a piezoelectric layer 70 with a thickness of 1.3 μm was formed.

Then, on the substrate 10 with the layers from the elastic film 51 to the piezoelectric layer 70 thereon, a Pt film (second electrode 80) was formed by sputtering with a Pt target, completing sample 1 as a piezoelectric element 300 according to Embodiment 1. The amount of Pb added in excess (Pb overage) in the piezoelectric layer 70 of sample 1 was 14 mol %.

Fabrication of Samples 2 to 7

A piezoelectric layer 70 was formed and each of samples 2 to 7 was obtained in the same way as in the fabrication of sample 1 except that the precursor solution was prepared so that the Pb content of the piezoelectric layer 70 would satisfy x=1.8, 2.0, 2.2, 1.2, 2.4, and 3.0. The Pb overages in the piezoelectric layer 70 of samples 2 to 7 were 18 mol %, 20 mol %, 22 mol %, 12 mol %, 24 mol %, and 30 mol %, respectively.

Fabrication of Sample 8

A piezoelectric layer 70 was formed and sample 8 was obtained in the same way as in the fabrication of sample 2 except that in the firing, the annealing was performed at 650° C. The Pb overage in the piezoelectric layer 70 of sample 8 was 18 mol %.

The Pb overages [mol %] of samples 1 to 8 are each presented in Table 1.

TABLE 1

| Sample | Pb overage [mol %] | Change in $P_m$ [%] | Current density [μAcm$^{-2}$] | Activation energy [eV] |
|---|---|---|---|---|
| 1 | 14 | +1.8 | 11.3 | 0.59 |
| 2 | 18 | +0.1 | 2.74 | 0.48 |
| 3 | 20 | −2.0 | 5.76 | 0.50 |
| 4 | 22 | −4.8 | 6.49 | 0.57 |
| 5 | 12 | −4.2 | 7.45 | 0.55 |
| 6 | 24 | −8.0 | 24.7 | 0.68 |
| 7 | 30 | −6.9 | 31.1 | 0.68 |
| 8 | 18 | — | 134 | 1.24 |

Fatigue Measurement

On samples 1 to 7, pulsating fatigue measurement (fatigue measurement) was performed using TOYO Corporation "FCE-1A." The fatiguing pulses were a 50-kHz square wave with VL=0 V and VH=+25 V, and reading was performed using a 1 kHz triangular wave with VL=−25 V and VH=+25 V. As mentioned herein, the change in $P_m$ [%] is defined as the amount of polarization at 25 V applied voltage.

Figure 15:
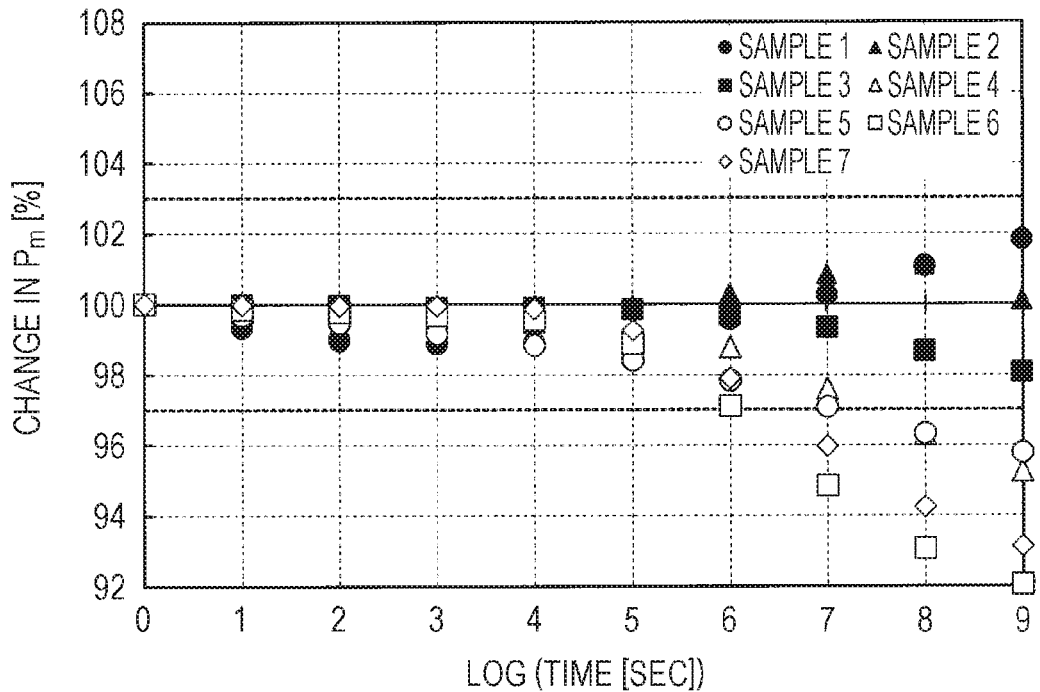
FIG. 15 is a graph that shows the results of fatigue measurement performed on samples 1 to 7.

FIG. 15 is a graph that shows the results of fatigue measurement performed on samples 1 to 7. This graph presents the percent change in $P_m$ as a function of the number of pulses applied. As shown in FIG. 15, the percent change in $P_m$ of samples 1 to 7 increased or decreased with the application of fatiguing pulses. In general, a change in the $P_m$ of a piezoelectric element 300 leads to a change in piezoelectric constant. Thus, it is desirable that the percent change in $P_m$ fall within a certain range, for example within ±3% (the change in $P_m$ in FIG. 15 be between 97% and 103%). In relation to this, the percent changes in $P_m$ at pulse counts of 10$^0$ pulses and 10$^9$ pulses in FIG. 15 were compared. The differences are presented in Table 1. As shown in Table 1, samples 1 to 3, which exhibited a percent change in $P_m$ within +3%, experience only small changes in long-term characteristics as a piezoelectric element 300.

I-t Measurement

On samples 1 to 7, current-time curve (I-t curve) measurement (I-t measurement) was performed using Hewlett-Packard "4140B." This measurement was carried out under the conditions of a heating temperature of 150° C. and a voltage applied of 40 V. Although not shown, sample 1 exhibited a typical current-time curve, in which the amount of current initially decreased over time and then, after a certain time, the trend in current turned upward. The time at which a downward trend in current turns upward is herein referred to as "relaxation time," and the amount of current (current density [μAcm$^{-2}$]) at this relaxation time as "relaxation current."

Figure 16:
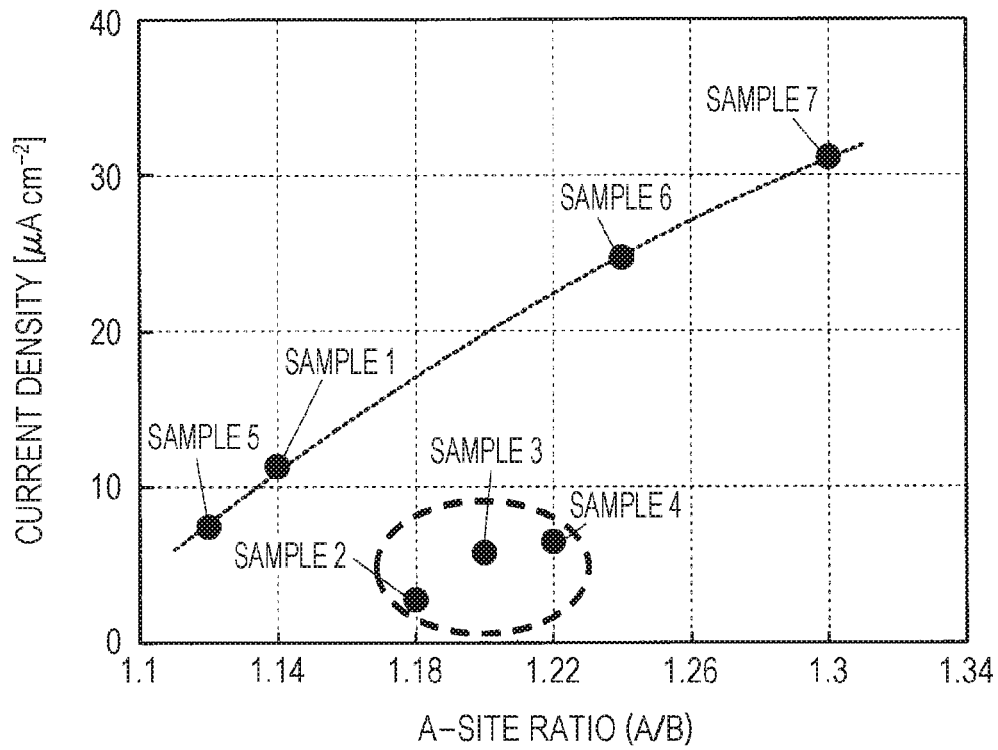
FIG. 16 is a graph that shows the Pb-content dependence of relaxation current in samples 1 to 7.

FIG. 16 is a graph that shows the Pb-content dependence of relaxation current in samples 1 to 7. The relaxation current (current density [μAcm$^{-2}$]) values in FIG. 16 are presented in Table 1. In FIG. 16, the result for sample 8 is not shown.

In general, PZT is produced with Pb in excess of the stoichiometric amount derived from ABO$_3$ as a countermeasure against the evaporation of Pb during the production process. It is well known that the excess of Pb exists at the B-site and becomes a p-type dopant. The amount of current that the PZT leaks is therefore proportional to the Pb overage, if no other factor contributes. In samples 1 to 7, presented in FIG. 16 and Table 1, however, some compositions result in a decrease in current density (leakage level) as seen in samples 2 to 4.

The inventors, however, believe that this result tends to occur when the factors other than composition (e.g., firing temperature) are constant. As shown in Table 1, sample 8, fabricated under the same conditions as sample 2 except that the firing temperature was 650° C. (a temperature acceptable for crystal growth), tended to exhibit a higher current density (leakage level) than the other samples.

The A-site ratio (A/B) in FIG. 16 is the ratio of the A-site (Pb) to the B-site (Zr+Ti) in formula (7), and (A/B)=(x/1). If sample 1, whose Pb overage, in Table 1, was 14 mol %, is taken as an example, the A-site ratio (A/B) is 1.14.

Analysis of Arrhenius Plot

To analyze the above phenomenon observed in samples 2 to 4, I-t measurement was performed with heating temperatures of 120° C. and 180° C., and the activation energy was calculated from the measured relaxation currents. The electrical conductivity of a typical semiconductor (insulator) follows the Arrhenius equation, given as formula (8).

$$\sigma = A\exp(-Ea/k_B T) \quad (8)$$

In formula (8), σ is electrical conductivity (electroconductivity), A is frequency factor, Ea is activation energy, $k_B$ is the Boltzmann constant, and T is absolute temperature. Since Ea, $k_B$, and A are constants, the logarithm of the Arrhenius equation is a linear expression of 1/T, as shown in formula (9).

$$\ln \sigma = (-Ea/k_B) \times (1/T) + \ln A \quad (9)$$

Figure 17:
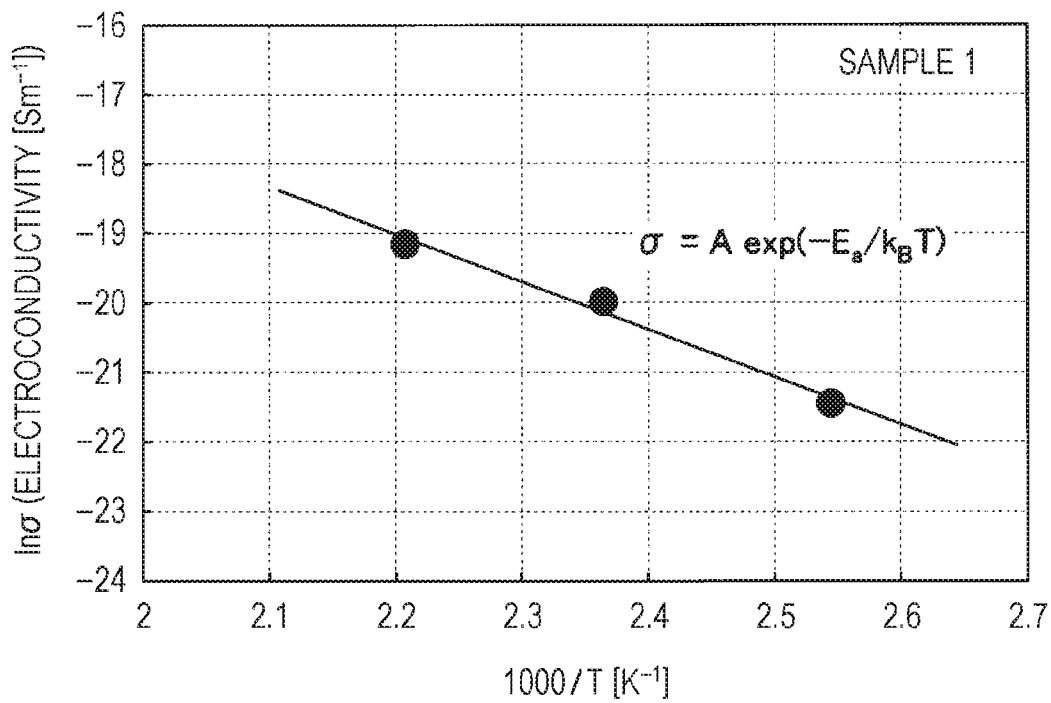
FIG. 17 is a graph that shows an Arrhenius plot of sample 1.

Therefore, creating a graph in which the vertical axis represents ln σ and the horizontal axis is 1/T (Arrhenius plot) and finding its slope gives the activation energy. FIG. 17 is a graph that shows an Arrhenius plot of sample 1. As shown in FIG. 17, the relaxation current of sample 1 exhibited a linear correlation that followed the Arrhenius law. Although not shown, the activation energy was calculated for samples 2 to 8, too, in the same way as for sample 1.

Figure 18:
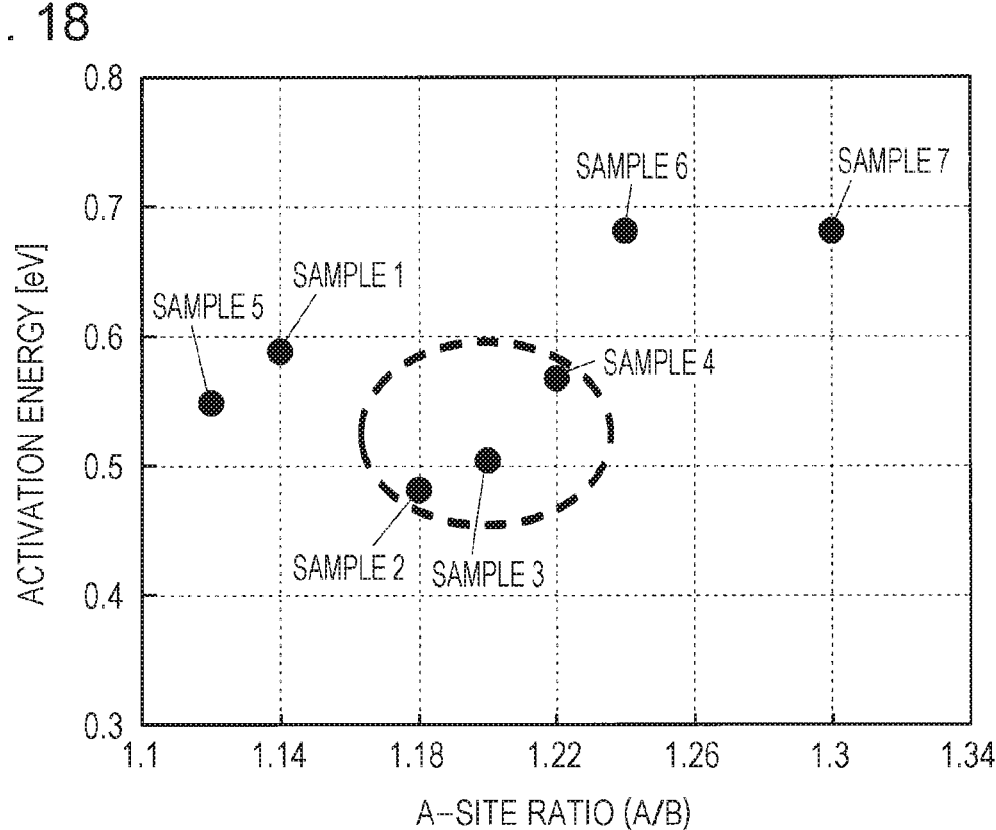
FIG. 18 is a graph that shows the Pb-content dependence of activation energy in samples 1 to 7.

FIG. 18 is a graph that shows the Pb-content dependence of activation energy in samples 1 to 7. The activation energy values of samples 1 to 8 in FIG. 18, calculated from Arrhenius plots, are presented in Table 1. In FIG. 18, the result for sample 8 is not shown.

As can be seen from FIG. 18, the activation energy was specifically low in samples 2 to 4. This indicates that in FIG. 18, a conduction band other than that resulting from excessive Pb contributed.

Figure 19:
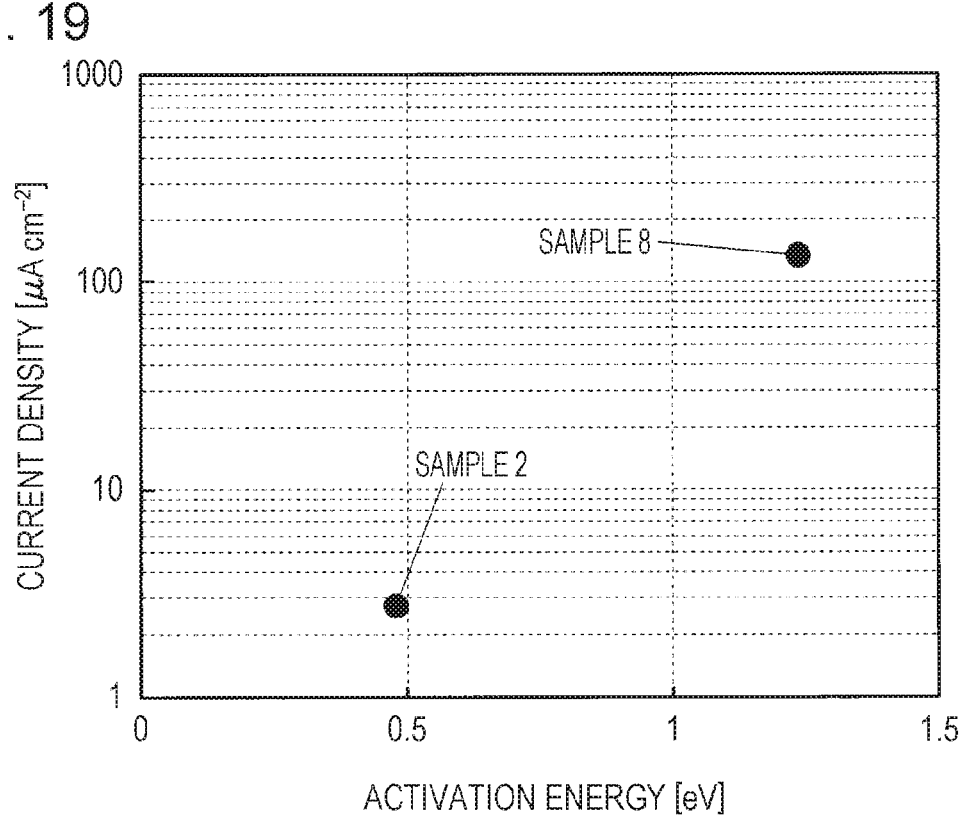
FIG. 19 is a graph that shows the activation-energy dependence of relaxation current in samples 2 and 8.

FIG. 19 is a graph that shows the activation-energy dependence of relaxation current in samples 2 and 8. This graph presents the activation-energy dependence of current density (leakage level) in samples 2 and 8, which shared the same composition and differed in firing temperature. As can be seen from FIG. 19, the current density (leakage level) is reduced with lower activation energy, even with the same composition.

From these results, in samples 2 to 4, it was shown that intentionally lowering the activation energy is effective in reducing the current density (leakage level).

Fabrication of Samples 9 to 12

A piezoelectric layer 70 was formed and each of samples 9 to 12 was obtained in the same way as in the fabrication of sample 1 except that the thickness of the piezoelectric layer 70, denoted by $T_p$, and the total thickness of the elastic film 51 and first electrode 60, denoted by $T_b$, were as in Table 2. The results of the calculations of the $T_p$-to-$T_b$ relationship ($T_p/T_b$) are also presented in Table 2.

TABLE 2

| Sample | $T_p$ [μm] | $T_b$ [μm] | $T_p/T_b$ | $F_a$ [MHz] | Electromechanical coupling coefficient |
|---|---|---|---|---|---|
| 9 | 1.3 | 1.6 | 0.81 | 5.93 | 0.292 |
| 10 | 0.6 | 1.6 | 0.38 | 5.82 | 0.262 |
| 11 | 0.9 | 1.6 | 0.56 | 5.99 | 0.292 |
| 12 | 2.0 | 1.6 | 1.25 | 5.92 | 0.280 |

XRD Measurement

The piezoelectric layer 70 of samples 9 to 12 was structurally analyzed at room temperature by X-ray diffraction (XRD) using Bruker AXS "D8 Discover." In this measurement, the X-ray source was CuKα, and the detector was a two-dimensional detector (GADDS). The measurement revealed that in samples 9 to 12, the piezoelectric layer 70 was (100)-oriented. The (100) orientation as mentioned herein is an orientation with Miller indices determined with the $ABO_3$ perovskite structure regarded as cubic crystals and therefore is different from the actual crystal structure. For example, in a cubic crystal structure in samples 9 to 12, the (100) orientation means that one or both of the (100) and (001) planes are aligned perpendicular to the substrate 10.

Shape Observation and Length Measurement

In general, the shape into which an actuator is worked and the effective area of the electrodes have great impact on the vibration properties of the actuator. Thus, the shape of samples 9 to 12 was subjected to observation and measurement of lengths under an optical microscope. The shape of samples 9 and 12 was as predetermined, with no abnormalities that would affect characteristics. The analysis of the results of the subsequent measurements therefore did not need to consider structural factors.

Measurement of Cross-Sectional Shape

For the measurement of a cross-sectional shape, samples 9 to 12 were observed under an electron microscope (Hitachi, Ltd. Scanning Transmission Electron Microscope HD 2000). The cross sections measured were created by focused ion beam (FIB). The film structure was as predetermined, and no meaningful difference was observed among samples 9 to 12 except for the thickness $T_p$ of the piezoelectric layer 70. Table 2 presents the thickness $T_p$ of the piezoelectric layer 70, total thickness $T_b$ of the elastic film 51 and first electrode 60, and $T_p$-to-$T_b$ relationship ($T_p/T_b$) determined through the FIB-STEM observation.

Impedance Evaluation and the Calculation of Electromechanical Coupling Coefficient On samples 9 to 12, the frequency dependence of impedance at room temperature (25° C.) was measured using Hewlett-Packard "4294A." The voltage applied was 5±0.5 V, and the frequencies at which the impedance was measured ranged from 5 MHz to 9 MHz.

Figure 20:
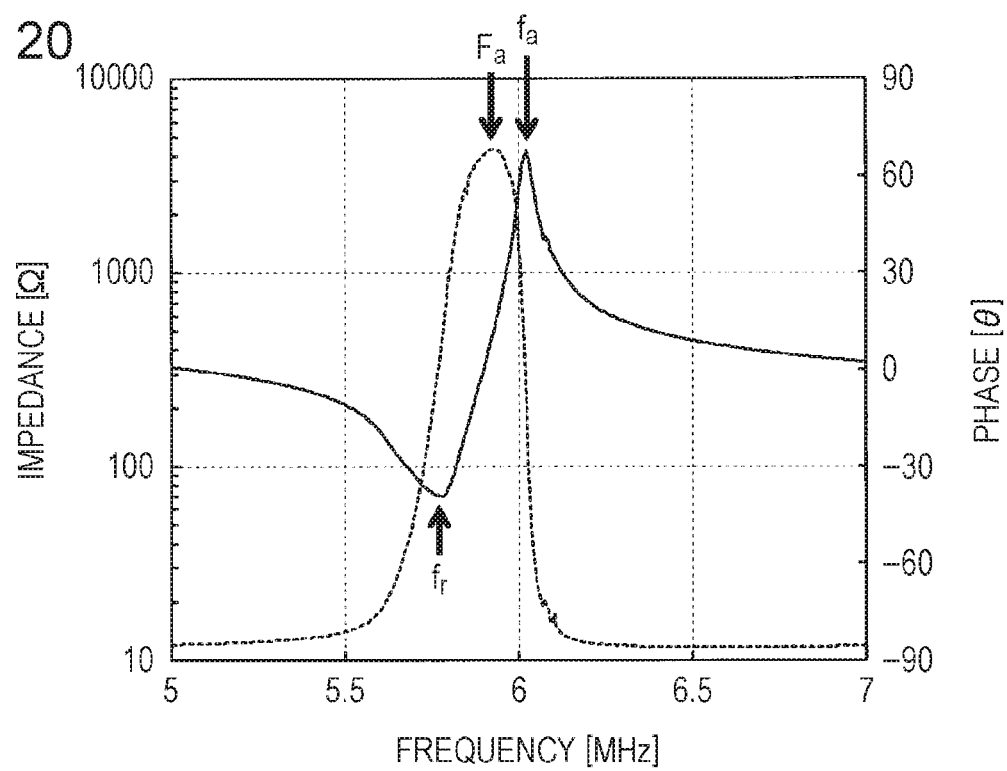
FIG. 20 is a graph that shows the results of measurement of the impedance of sample 9.

FIG. 20 is a graph that shows the results of measurement of the impedance of sample 9. As shown in FIG. 20, a single resonance and a resonance peak were found. At the same time, piezoelectric actuator equipment equipped with sample 9 was driven at this resonance frequency, and the resulting vibrations were measured using a laser Doppler vibrometer. This measurement found that the resonance peak in FIG. 20 was the deformation mode of the diaphragm. Although not shown, impedance measurement was performed similarly on samples 10 to 12, too. In sample 9, the elastic film 51 and first electrode 60 function as a diaphragm.

Figure 21:
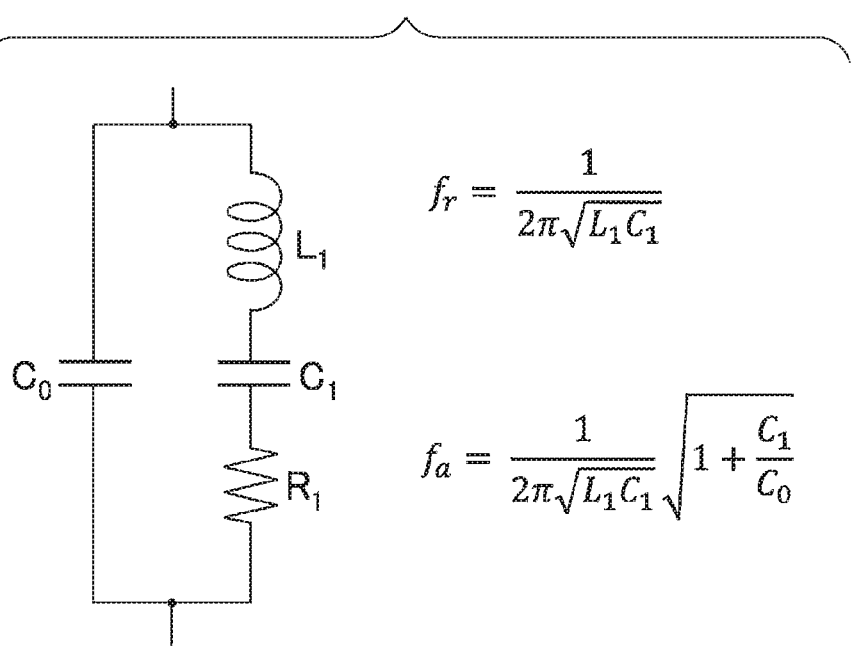
FIG. 21 is a diagram that illustrates an equivalent-circuit model and the definition of parameters.

FIG. 21 is a diagram that illustrates an equivalent-circuit model and the definition of parameters. The inventors performed a preliminary study, and the results confirmed that the resistance and parasitic capacitance (stray capacitance) of the tester and wiring were negligible compared with the capacitance and impedance of the piezoelectric actuator equipment. The electromechanical coupling coefficient was calculated among pieces of piezoelectric actuator equipment equipped with samples 9 to 12 using the equivalent-circuit model illustrated in FIG. 21. In the calculations, the frequency, in FIG. 20, at which the impedance bottomed out was defined as $f_r$, the frequency at which the impedance peaked as $f_a$, and the frequency at which the phase peaked as $F_a$. $F_a$=5.9±0.1 MHz for all pieces of piezoelectric actuator equipment, demonstrating that the changes in resonance frequency depending on film thicknesses were negligible. The calculated electromechanical coupling coefficient and $F_a$ are presented in Table 2.

Note that in the equivalent-circuit model in FIG. 21, the damped capacitance $C_0$ is a capacitance determined by the dielectric constant of the transducer and the dimensions of the electrodes and represents the component of current that flows in the transducer. The equivalent inductance $L_1$ and equivalent capacitance $C_1$ represent piezoelectric mechanical vibration, which is determined by factors such as the vibration mode of the transducer and the dimensions, elastic constant, and piezoelectric constant of the element, and the resonance resistance $R_1$ represents the loss of mechanical vibration.

The calculations of the electromechanical coupling coefficient were based on formula (10). In formula (10), k represents the electromechanical coupling coefficient.

$$k^2 = (f_a^2 - f_r^2)/f_a^2 \qquad (10)$$

Figure 22:
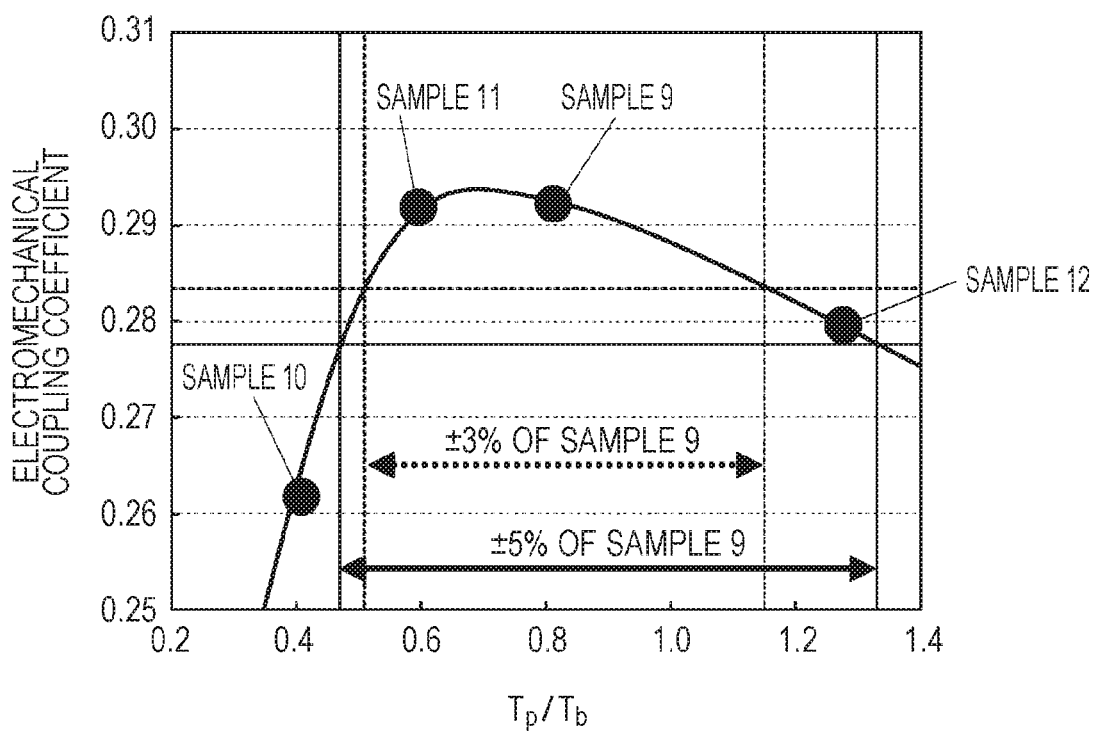
FIG. 22 is a graph that shows the film-thickness dependence of the electromechanical coupling coefficient in samples 9 to 12.

FIG. 22 is a graph that shows the film-thickness dependence of the electromechanical coupling coefficient in samples 9 to 12. As shown in FIG. 22 and Table 2, samples 9 and 11 exhibited similar electromechanical coupling coefficients, demonstrating that a $T_p/T_b$ ratio outside a predetermined range results in a decrease in electromechanical coupling coefficient. This is because of a trade-off between the force for deforming the diaphragm and the position of the center of stress in the piezoelectric layer 70. As can be seen from these results, the region in which the displacement of a piezoelectric actuator is within ±5% based on the electromechanical coupling coefficient of sample 9 is when $T_p/T_b$ falls within the range represented by formula (11). Likewise, the region in which the displacement of a piezoelectric actuator is within ±3% based on the electromechanical coupling coefficient of sample 9 is when $T_p/T_b$ falls within the range represented by formula (12).

$$0.47 < T_p/T_b < 1.33 \tag{11}$$

$$0.51 < T_p/T_b < 1.15 \tag{12}$$

Other Embodiments

Although the above embodiments describe a liquid ejecting head for a liquid ejecting apparatus as an example of a piezoelectric element-based device, the scope of this aspect of the invention is not limited to this. The described example of a liquid ejecting head is an ink jet recording head, but naturally, this aspect of the invention is also applicable to liquid ejecting heads that eject a liquid other than ink. Examples of liquid ejecting heads that eject a liquid other than ink include a colorant ejecting head, which is used to form color filters, for example of a liquid crystal display; an organic EL material ejecting head, which is used to form a light-emitting layer and an electron transport layer of an organic EL display; an electrode material ejecting head, which forms an electrode pattern by applying an electrode precursor solution; a curable material ejecting head, which repeats the ejection of a material and light-induced or thermal curing of the material to build a three-dimensional object (3D printing); a piezoelectric material ejecting head, which forms a piezoelectric element pattern through the application and heat treatment of a piezoelectric material precursor solution; and a bioorganic substance ejecting head, which is used in the production of a biochip.

The piezoelectric element and piezoelectric element-based device according to aspects of the invention are suitable for piezoelectric actuator equipment by virtue of their high piezoelectric properties. Specific examples of piezoelectric actuator equipment include an ultrasonic transmitter, an ultrasonic motor, a vibrating duster, a piezoelectric transducer, a piezoelectric speaker, a piezoelectric pump, a thermoelectric transducer, and a piezoelectric transducer.

The piezoelectric element and piezoelectric element-based device according to aspects of the invention are suitably applicable to piezoelectric sensor elements by virtue of their high piezoelectric performance. Specific examples of sensor elements include an ultrasonic detector (ultrasonic sensor), an angular velocity sensor (gyro sensor), an acceleration sensor, a vibration sensor, a slope sensor, a pressure sensor, a crash sensor, a human detection sensor, an infrared sensor, a terahertz sensor, a heat detection sensor (thermal sensor), a pyroelectric sensor, and a piezoelectric sensor. The piezoelectric element and piezoelectric element-based device according to aspects of the invention can also be applied to, for example, filters, such as a filter against infrared or other harmful radiation, an optical filter that works on a photonic crystal effect resulting from the formation of quantum dots, an optical filter that works on the interference of light in a thin film.

The piezoelectric element and piezoelectric element-based device according to aspects of the invention are suitably applicable to ferroelectric elements by virtue of their high ferroelectricity. Specific examples of ferroelectric elements include a ferroelectric random access memory (FeRAM), a ferroelectric field effect transistor (FeFET), a ferroelectric logic circuit (FeLogic), and a ferroelectric capacitor.

The piezoelectric element and piezoelectric element-based device according to aspects of the invention are suitably applicable to voltage-controlled optical elements because the domains can be controlled through the application of voltage. Specific examples of optical elements include a wavelength converter, an optical waveguide, a path-length modulator, a refractive index controller, and an electronic shutter mechanism.

The piezoelectric element and piezoelectric element-based device according to aspects of the invention are suitably applicable to pyroelectric elements by virtue of their good pyroelectric properties. The piezoelectric element and piezoelectric element-based device according to aspects of the invention can also be applied to, for example, robots in which an aforementioned motor is used as a drive source.

With regard to an ultrasonic measuring instrument equipped with an ultrasonic sensor, it is also possible to, for example, construct such an ultrasonic measuring instrument by combining a piezoelectric element according to an aspect of the invention with a control unit that measures a subject of detection using signals based on at least either of ultrasonic waves transmitted by the piezoelectric element according to an aspect of the invention and ultrasonic waves received by the piezoelectric element according to an aspect of the invention. Such an ultrasonic measuring instrument collects information about the position, shape, speed, etc., of a subject of measurement on the basis of the length of time between the time point at which the instrument transmits an ultrasonic wave and the time point at which the instrument receives an echo signal, a signal of the transmitted ultrasonic wave reflecting back off the subject of measurement, and in some such instruments, a piezoelectric element is used as an element for generating ultrasonic waves or an element for detecting echo signals. It is possible to provide an ultrasonic measuring instrument that has superior displacement properties as such an ultrasonic generating element or echo signal sensing element.

A configuration is possible in which, for example, the region through which the ultrasonic waves transmitted toward the subject of measurement and the ultrasonic waves reflected off the subject of measurement (echo signal) pass is on the side of the diaphragm opposite the piezoelectric element. This simplifies the structure on the side of the diaphragm opposite the piezoelectric element, securing a good region for the ultrasonic waves, etc., to pass through. The electrical regions, such as electrodes and wiring, and the regions in which the individual components are fastened by bonding together are kept away from the subject of measurement, helping prevent contamination and leakage current between these regions and the subject of measurement. Such an ultrasonic measuring instrument is therefore suitably applicable even to medical equipment for which contamination and leakage current are especially serious issues, such as ultrasonic diagnostic equipment (ultrasonic imaging system), a manometer, and an ophthalmotonometer.

It is preferred to join, to the substrate, a sealing plate for sealing a region including the piezoelectric element. This provides physical protection for the piezoelectric element and increases the strength of the ultrasonic sensor, resulting in increased structural stability. If a thin-film piezoelectric element is used, furthermore, joining such a sealing plate improves the handling of an ultrasonic sensor that includes this piezoelectric element.

Although in the above embodiments the openings are created in one-to-one correspondence to the piezoelectric elements, this is not the only possible configuration. Openings may be created in such a manner that one corresponds to multiple piezoelectric elements. For example, there may be openings each shared by a row of piezoelectric elements lined up in the scan direction (X direction), or alternatively all openings may be combined into one. Although providing such common openings each serving for multiple piezoelectric elements changes the state of vibration of the piezoelectric elements, it is possible to keep the same state of vibration as would be with separate openings for the piezoelectric elements, for example, a component for holding the areas of the diaphragm between the piezoelectric elements from the side of the diaphragm opposite the substrate.

Although the above embodiments describe CAV-structured flexural-deformation actuators formed by ICP etching by way of example, the structure does not need to be the described one as long as the piezoelectric elements operate using flexural deformation. Examples of possible structures include a CAV structure created by wet etching, a structure including a CAV pattern formed from photoresist, a structure including a diaphragm and a CAV pattern prepared separately and attached together, and a structure in which the diaphragm is a cantilever.

Figure 23:
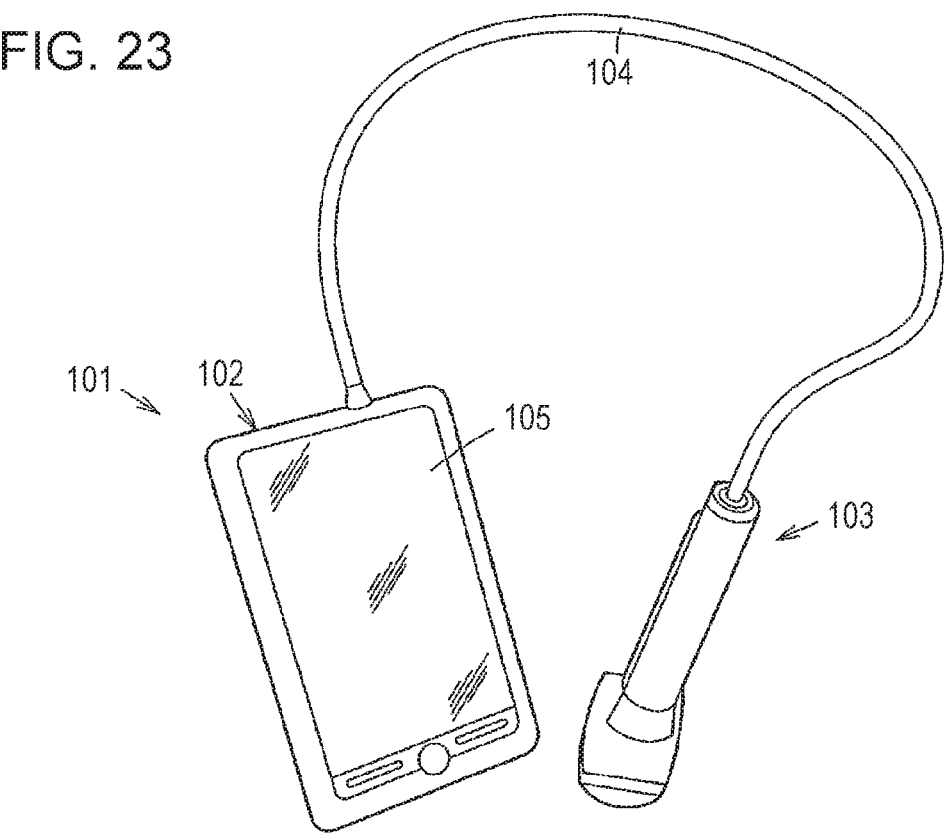
FIG. 23 is a perspective diagram that illustrates an example of an ultrasonic imaging system.
Figure 24:
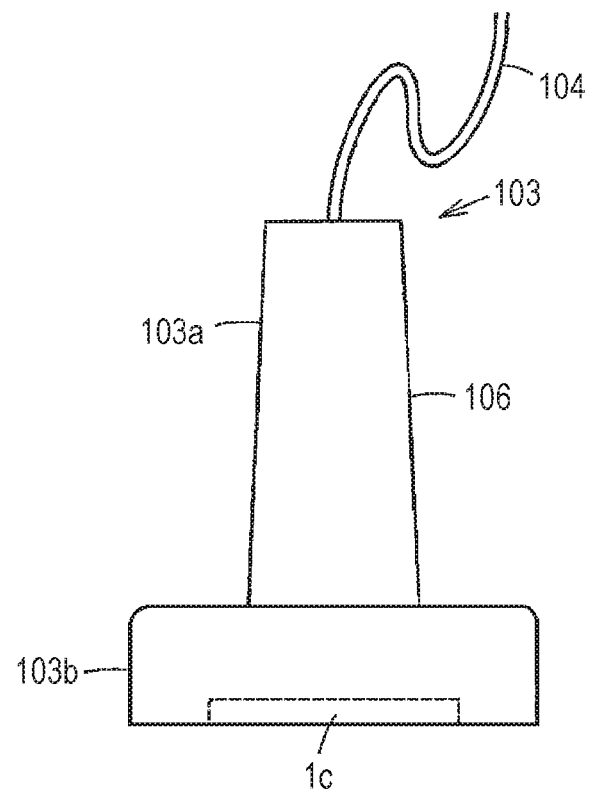
FIG. 24 is a front view of an example of an ultrasonic probe.

The following describes an example of electronic equipment in which an above-described ultrasonic sensor is used. In this embodiment, an ultrasonic imaging system is described as an example of electronic equipment, and an ultrasonic probe as an example of an ultrasonic device. FIG. 23 is a perspective diagram that schematically illustrates the structure of an example of an ultrasonic imaging system. FIG. 24 is a plan view of an ultrasonic probe.

As illustrated in FIG. 23, the ultrasonic imaging system 101 includes a system terminal 102 and an ultrasonic probe (probe) 103. The system terminal 102 and the probe 103 are connected with a cable 104. The system terminal 102 and the probe 103 exchange electrical signals through the cable 104. The system terminal 102 has a built-in display unit (display panel) 105. The screen of the display panel 105 is exposed on the surface of the system terminal 102. At the system terminal 102, an image is formed on the basis of ultrasonic waves transmitted from and detected by the ultrasonic sensor 1c of the probe 103 (see FIG. 24). The results of detection, in the form of an image, show up on the screen of the display panel 105.

As illustrated in FIG. 24, the probe 103 has an enclosure 106. In the enclosure 106, an ultrasonic sensor 1c is housed that includes a two-dimensional array, in the X and Y directions, of multiple ultrasonic elements 10c (see FIG. 14 and other drawings). The surface of the ultrasonic sensor 1c is exposed on the surface of the enclosure 106. The ultrasonic sensor 1c sends out ultrasonic waves through its surface and receives reflected ultrasonic waves. The main body 103a of the probe 103 can be fitted with a detachable probe head 103b. In this case, the ultrasonic sensor 1c may be built in the enclosure 106 of the probe head 103b.

What is claimed is:

1. A piezoelectric element comprising:
   a diaphragm;
   a first electrode on the diaphragm;
   a piezoelectric layer on the first electrode, the piezoelectric layer being a stack of a plurality of piezoelectric films; and
   a second electrode on the piezoelectric layer, wherein:
   the piezoelectric layer is made of a perovskite composite oxide containing lead, zirconium, and titanium and represented by a general formula $ABO_3$, with a molar ratio of an A-site to a B-site, A/B, in the perovskite composite oxide being 1.14 or more and 1.22 or less; and
   in current-time curve measurement, activation energy calculated from relaxation current using an Arrhenius plot is 0.6 [eV] or less, where the relaxation current is an amount of current at a time at which a downward trend in current turns upward.

2. The piezoelectric element according to claim 1, wherein:
   the molar ratio of the A-site to the B-site, A/B, in the perovskite composite oxide is 1.16 or more and 1.20 or less; and
   the activation energy is 0.5 [eV] or less.

3. The piezoelectric element according to claim 1, wherein:
   a relationship between a thickness $T_p$ of the piezoelectric layer and a total thickness $T_b$ of the diaphragm and first electrode satisfies formula (1); and
   electromechanical coupling coefficient k calculated from formula (2), where $f_a$ is a frequency [MHz] at which impedance peaks and $f_r$ is a frequency [MHz] at which the impedance bottoms out, is 0.278 or more.

$$0.47 < T_p/T_b < 1.33 \quad (1)$$

$$k^2 = (f_a^2 - f_r^2)/(f_a^2) \quad (2)$$

4. The piezoelectric element according to claim 3, wherein the relationship between the thickness of the piezoelectric layer, diaphragm, and first electrode satisfies formula (3), and the electromechanical coupling coefficient k calculated from formula (2) is 0.284 or more.

$$0.51 < T_p/T_b < 1.15 \quad (3)$$

5. A piezoelectric element-based device comprising a piezoelectric element according to claim 1.

6. A piezoelectric element-based device comprising a piezoelectric element according to claim 2.

7. A piezoelectric element-based device comprising a piezoelectric element according to claim 3.

8. A piezoelectric element-based device comprising a piezoelectric element according to claim 4.

* * * * *